(12) United States Patent
Kozikowski et al.

(10) Patent No.: US 6,350,758 B1
(45) Date of Patent: Feb. 26, 2002

(54) TROPANE DERIVATIVES AND METHOD FOR THEIR SYNTHESIS

(75) Inventors: Alan P. Kozikowski, Princeton, NJ (US); Gian Luca Araldi, Washington, DC (US)

(73) Assignee: Georgetown University, Washington, DC (US)

( * ) Notice: Subject to any disclaimer, the term of this patent is extended or adjusted under 35 U.S.C. 154(b) by 0 days.

(21) Appl. No.: 09/319,188

(22) PCT Filed: Dec. 2, 1997

(86) PCT No.: PCT/US97/21706

§ 371 Date: Sep. 14, 1999

§ 102(e) Date: Sep. 14, 1999

(87) PCT Pub. No.: WO98/24788

PCT Pub. Date: Jun. 11, 1998

Related U.S. Application Data
(60) Provisional application No. 60/032,231, filed on Dec. 2, 1996.

(51) Int. Cl.[7] .................. A61K 31/46; C07D 451/02
(52) U.S. Cl. .................. 514/304; 546/124; 546/127; 546/132
(58) Field of Search .................. 514/304; 546/124, 546/127, 132

(56) References Cited

U.S. PATENT DOCUMENTS
5,935,953 A * 8/1999 Kuhar et al. .............. 514/235.2

* cited by examiner

*Primary Examiner*—Charanjit S. Aulakh
(74) *Attorney, Agent, or Firm*—Schwegman, Lundberg, Woessner & Kluth, P.A.

(57) ABSTRACT

A compound of formula (I) wherein $R_1$–$R_6$ have any of the values defined in the specification are described, as well as pharmaceutical compositions comprising a compound of formula (I), and methods for preparing and using compounds of formula (I) are described.

(I)

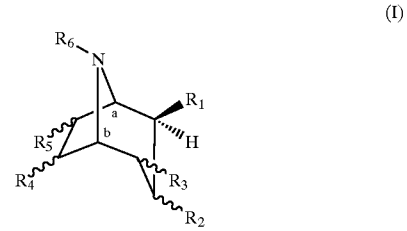

17 Claims, 8 Drawing Sheets

4a-d - EWG = CN
5a-d - EWG = SO₂Ph
6a-d - EWG = CO₂Et

| compd | R | R' | isomer | Mazindol Binding | | [³H]DA Uptake | | [³H]5HT Uptake | | ratio |
|---|---|---|---|---|---|---|---|---|---|---|
| | | | | IC₅₀* | Kᵢ* | IC₅₀* | Kᵢ* | IC₅₀* | Kᵢ* | 5HT/DA |
| | cocaine | | | | 280 | | 320 | | | |
| 15 | CO₂Me | H | 2β, 3β | 163.1 | 89.4 | 57.9 | 53.7 | 203.9 | 185.6 | 3.4 |
| 16 | CO₂Me | Me | 2β, 3β | 10.5 | 5.8 | 7.5 | 6.92 | 25.5 | 23.2 | 3.36 |
| 21 | n-Pr | H | 2β, 3β | 23.1 | 12.2 | 7.5 | 6.89 | 95.4 | 86.8 | 12.6 |
| 47 | n-Pr | H | 2β, 3α | 141.4 | 74.9 | 32.6 | 30.2 | 427.6 | 389.4 | 12.9 |
| 22 | n-Pr | Me | 2β, 3β | 2.97 | 1.6 | 1.19 | 1.10 | 11.3 | 10.3 | 9.35 |
| 51 | n-Pr | Me | 2β, 3α | 18.2 | 8.9 | 12.7 | 11.8 | 54.8 | 50.1 | 4.25 |
| 23 | n-Bu | Me | 2β, 3β | 3.43 | 1.82 | 1.42 | 1.31 | 16.5 | 15.1 | 11.5 |
| 52 | n-Bu | Me | 2β, 3α | 21.6 | 11.4 | 10.9 | 10.1 | 55.8 | 50.9 | 5.07 |
| 48 | Ph | H | 2β, 3β | 96.5 | 49.9 | 31.1 | 28.9 | 1200 | 1100 | 38.1 |
| 49 | Ph | H | 2β, 3α | 26.6 | 13.8 | 12.6 | 11.7 | 822.5 | 752.7 | 69.3 |
| 50 | Ph | Me | 2β, 3β | 4.98 | 2.58 | 3.09 | 2.87 | 80.8 | 73.77 | 25.7 |
| 37 | Ph | Me | 2β, 3α | 5.55 | 2.87 | 4.48 | 4.16 | 314.1 | 286.9 | 64.6 |

*Data are expressed in nM

TROPANE DERIVATIVES AND METHOD FOR THEIR SYNTHESIS

This application claims benefit of Provisional application No. 60/032,231, filed Dec. 2, 1996.

BACKGROUND OF THE INVENTION (R)-Cocaine or (−)-cocaine is a plant alkaloid purified from the leaves of *Erythroxylon coca* and has been a subject of scientific investigation since the late 1800s. It is one of the eight possible stereoisomeric forms of methyl 3-(benzoyloxy)-8-methyl-8-azabicyclo [3.2.1]octane-2 carboxylate. Cocaine has many physiological effects. It is a local anesthetic, and this property is responsible for its early legitimate use in medicine. However, many newer compounds have been developed that are superior to cocaine for this purpose. Cocaine is also a powerful vasoconstrictant and, as such, has some current use in medicine during nasal or throat surgery where control of bleeding is desired. Cocaine also has very potent effects on the sympathetic nervous system, and it is well known to increase heart rate and blood pressure.

In both animals and humans, cocaine is one of the most reinforcing drugs known, which has given rise to a serious cocaine abuse epidemic in the United States over the last 10–15 years (see e.g., Musto, *Sci. Amer.*, 256, 40 (1991)). From the point of view of drug abuse, the most relevant effects of the drug include its ability to produce euphoria and its reinforcing effect. In addition to being a powerful reinforcer, cocaine also has properties common to other drugs subject to abuse. For example, tolerance occurs to some of its effects, and its psychological withdrawal syndrome takes place over a long time period, which includes periods of craving during which relapse to drug use often occur (see, Gawin et al., *Arch. Gen. Psychiatry*, 43, 107 (1986)).

Over the past 10 years, there have been significant advances in understanding the mechanism of action of cocaine. The development of drug self-administration as a useful animal model for reinforcing properties has led to exploration of many of the physiological, neurochemical, neuroanatomical, and pharmacological correlates (Griffiths, in *Advances in Substance Abuse*, Vol., 1, N. K. Mello, ed., UAI Press Inc., Greenwich Conn. (1980) at pages 1–90)).

Several studies have shown that cocaine binds to the dopamine transporter and inhibits dopamine transport (Kubar et al., *NIDA Research Monograph* (1988) at pages 14–22). In addition, drugs that are potent in maintaining self-administration, such as nomifensine, methylphendiate and mazindol, are also potent inhibitors of binding at the transport site for dopamine, whereas compounds that are weak in self-administration studies are correspondingly weak inhibitors of the binding site. For example, Ritz et al. (*Science*, 237 1249 (1987)) showed that the relative ability of several compounds to displace [$^3$H]mazindol binding to the dopamine transporter from rat striatum was correlated to drug self-administration studies in nonhuman primates. Similarly, Berman et al. (*J. Pharmacol. Exp. Ther.*, 251, 150 (1989)) found a good correlation between displacement of [$^3$H]-cocaine binding to the transporter and drug self-administration behavior in squirrel monkeys. The most potent compounds in binding and behavioral studies reported from both investigations were 3β-phenyltropane-2β-carboxylic acid methyl ester and 3β-(p-fluorophenyl) tropane-2β-carboxylic acid methyl ester (Clark et al., *J. Med. Chem.*, 16, 1260 (1973)).

Only a limited number of cocaine analogs have been available to study the structural requirements for binding to the dopamine transporter and for cocaine-like reinforcing properties. For example, Carroll et al. (*J. Med. Chem.*, 34, 2719 (1991); *Eur. J. Pharm.*, 184, 329 (1990)) synthesized and measured the binding affinity of a number of new 3β-(p-substituted phenyl)tropane-2β-carboxylic acid methyl esters and measured their ability to inhibit the binding of 0.5 nM [$^3$H]-3β-(p-fluorophenyl)tropane-2β-carboxylic acid methyl ester to the dopamine transport site of rat striata. The iodo- and chloro-substituted derivatives were found to have a potency of approximately 80 times that of (−)-cocaine in this in vitro assay. Carroll et al. (*J. Med. Chem.*, 35, 969 (1992)) proposed that specific hydrogen bond donor groups are present within the cocaine recognition site which bind to the 2-carbomethoxy group.

However, despite some success, a need exists for novel analogs of cocaine. Such compounds may exhibit enhanced analgesic and/or vasoconstrictive properties, or potentially be more selective than (−)-cocaine; or such analogs may inhibit the uptake of dopamine or serotonin and, therefore, be useful for treating a disease or condition such as Parkinson's disease, depression, or obesity. Such compounds may also be useful for treating cocaine abuse. A need also exists for additional methods to synthesize cocaine analogs.

Additionally, a need exists for cocaine analogs which can be employed to further characterize the cocaine binding site(s), and to assist in the development of additional specific cocaine binding site agonists and antagonists.

SUMMARY OF THE INVENTION

The present invention provides a compound of formula (I):

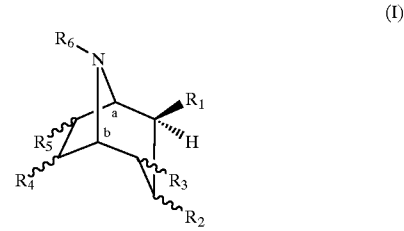

wherein $R_1$ is hydrogen, aryl, aryl($C_1$–$C_4$)alkyl, ($C_1$–$C_4$)alkyl, $OR_7$, or $N(R_8)_2$;

$R_2$ is aryl or aryl($C_1$–$C_4$)alkyl;

$R_3$ is hydrogen, ($C_1$–$C_4$)alkyl, ($C_2$–$C_4$)alkenyl or ($C_2$–$C_4$) alkynyl;

$R_4$ and $R_5$ are independently hydrogen, halo, CN, $OR_9$, $COOR_{10}$, arylSO$_2$—, or —CH$_2$NHR$_{11}$;

$R_6$ is hydrogen, ($C_1$–$C_4$)alkyl, ($C_1$–$C_4$)alkenyl, ($C_1$–$C_4$) alkynyl, aryl, or aryl($C_1$–$C_4$)alkyl;

$R_7$ is hydrogen, ($C_1$–$C_4$)alkyl, ($C_1$–$C_5$)alkanoyl, arylcarbonyl or aryl ($C_1$–$C_5$)alkanoyl;

each $R_8$ is independently hydrogen, ($C_1$–$C_4$)alkyl, ($C_1$–$C_4$)alkanoyl, aryl, aryl($C_1$–$C_4$)alkyl, or arylcarbonyl;

$R_9$ is hydrogen, ($C_1$–$C_4$)alkyl, ($C_1$–$C_5$)alkanoyl, or arylcarbonyl;

$R_{10}$ is hydrogen or ($C_1$–$C_4$)alkyl; and $R_{11}$ is hydrogen or ($C_1$–$C_4$)alkyl;

wherein any aryl in $R_1$, $R_2$, and $R_6$–$R_9$ may optionally be substituted with 1, 2, or 3 substituents independently selected from the group consisting of halo (preferably I or Cl), $CF_3$, $(C_1-C_4)$alkoxy, $(C_1-C_4)$alkyl, $(C_1-C_4)$ alkenyl, $(C_1-C_4)$alkynyl, amino, nitro cyano, and aryl;

or a pharmaceutically acceptable salt thereof.

The present invention also provides a method of synthesizing a compound of formula (III):

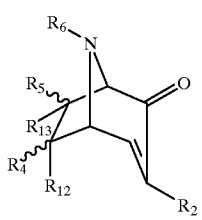

(III)

wherein $R_2$ is aryl or aryl$(C_1-C_4)$alkyl;

$R_4$ and $R_5$ are independently hydrogen, halo, CN, $OR_9$, $COOR_{10}$, —$CH_2NHR_{11}$, or a chiral auxiliary;

$R_6$ is hydrogen, $(C_1-C_4)$alkyl, $(C_1-C_4)$alkenyl, $(C_1-C_4)$alkynyl, aryl, or aryl$(C_1-C_4)$alkyl;

$R_9$ is hydrogen, $(C_1-C_4)$alkyl, $(C_1-C_5)$alkanoyl, or arylcarbonyl;

$R_{10}$ is hydrogen or $(C_1-C_4)$alkyl;

$R_{11}$ is hydrogen or $(C_1-C_4)$alkyl; and $R_{12}$ and $R_{13}$ are each hydrogen; or one of $R_{12}$ and $R_{13}$ is hydrogen, and the other is a chiral auxiliary (such as for example a (+)-(R)-p-tolylsulfinyl, or a (−)-(S)-p-tolylsulfinyl substituent).

wherein any aryl in $R_2$, $R_6$ and $R_9$ may optionally be substituted with 1, 2, or 3 substituents independently selected from the group consisting of halo (preferably I or Cl), $CF_3$, $(C_1-C_4)$alkoxy, $(C_1-C_4)$alkyl, $(C_2-C_4)$alkenyl, $(C_2-C_4)$alkynyl, amino, nitro cyano, or aryl;

comprising reacting a compound of formula (IV):

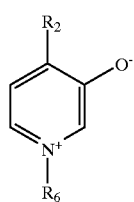

(IV)

with a compound of formula $R_4CH_2=CHR_5$. Preferably, the reaction is conducted with heating in a suitable organic solvent, i.e., under reflux conditions.

The method of the invention may further comprise reacting the compound of formula (III) with $R_3$—MgBr, where $R_3$ is $(C_1-C_4)$alkyl, $(C_2-C_4)$alkenyl or $(C_2-C_4)$alkynyl; a source of Cu(I), and a hydroxy protecting reagent such as $((C_1-C_4)$alkyl$)_3$SiCl followed by removal of the protecting group, to yield a compound of formula (V):

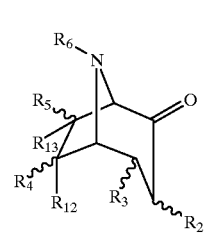

(V)

According to the invention, the method further comprises reducing the keto group in the compound of formula (V) to yield a compound of formula (VI):

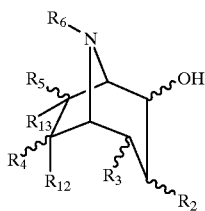

(VI)

and reacting the compound of formula (VI) with an anhydride of the formula $CH_3C(O)O$—$R_7$, where $R_7$ is $(C_1-C_5)$ alkanoyl, arylcarbonyl or aryl $(C_1-C_5)$alkanoyl to yield a compound of formula (I): wherein $R_1$ is $OR_7$.

According to the invention, for a compound of formula (III, IV, or V) wherein one of $R_{12}$ and $R_{13}$ is hydrogen and the other is a chiral auxiliary, the method may further comprise removing the chiral auxiliary to give a corresponding compound of formula (III, IV, or V) wherein $R_{12}$ and $R_{13}$ are each hydrogen.

The invention further provides a method of synthesizing a compound of formula (X):

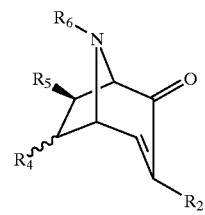

(X)

wherein $R_2$ is aryl or aryl$(C_1-C_4)$alkyl;

$R_4$ and $R_5$ are hydrogen or aryl$SO_2$—, provided that one of $R_4$ or $R_5$ is H and the other is aryl$SO_2$—; and $R_6$ is hydrogen, $(C_1-C_4)$alkyl, $(C_2-C_4)$alkenyl, $(C_2-C_4)$alkynyl, aryl, or aryl$(C_1-C_4)$alkyl;

wherein any aryl in $R_2$ or $R_6$ may optionally be substituted with 1, 2, or 3 substituents independently selected from the group consisting of halo (preferably I or Cl), $CF_3$, $(C_1-C_4)$alkoxy, $(C_1-C_4)$alkyl, $(C_2-C_4)$alkenyl, $(C_2-C_4)$alkynyl, amino, nitro cyano, and aryl;

comprising reacting a compound of formula (IV):

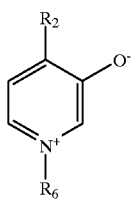

(IV)

with CH$_2$=CH—SO$_2$aryl.

DETAILED DESCRIPTION

Figure 1:
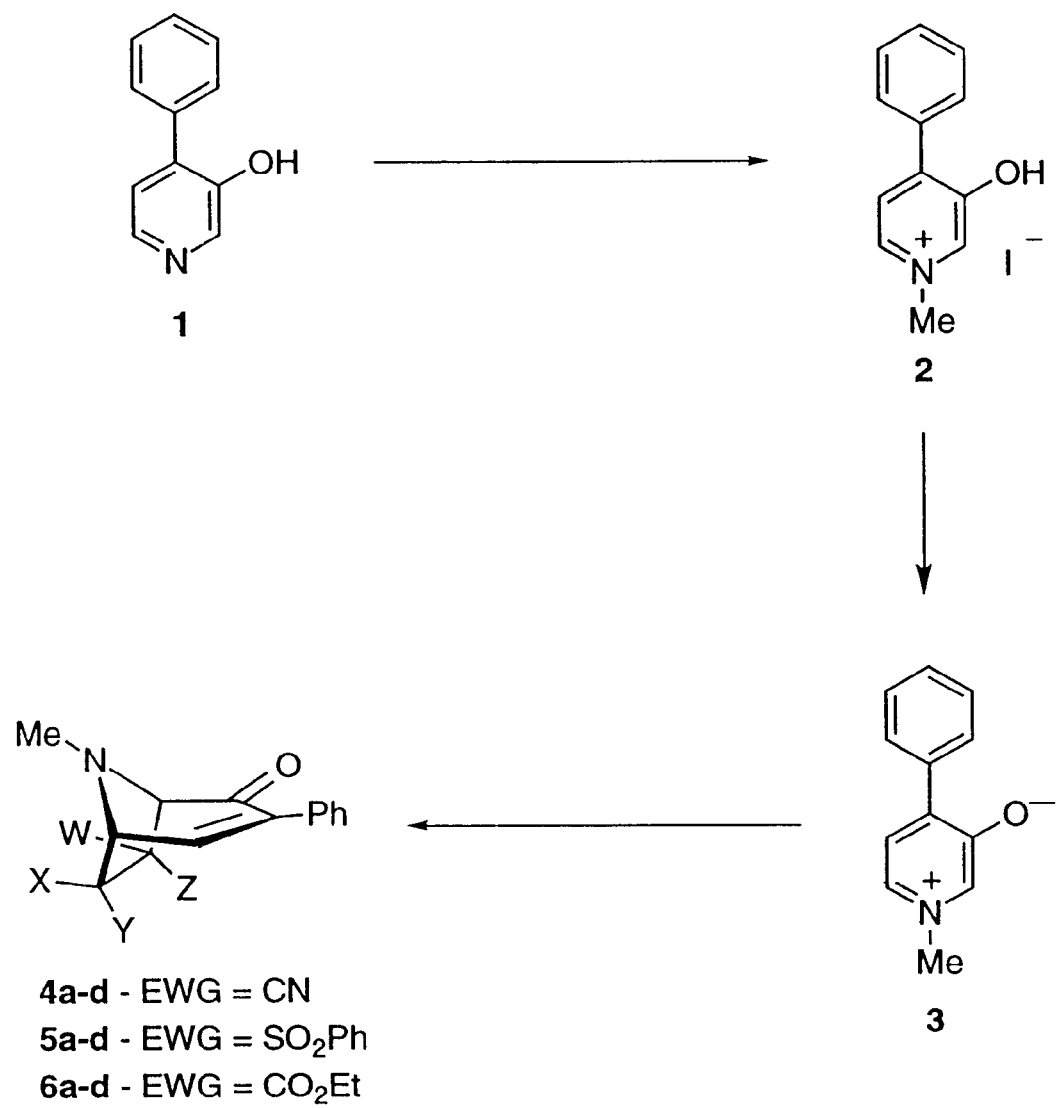
FIG. 1 illustrates the synthesis of intermediates useful for preparing compounds of formula (I).

The following definitions are used, unless otherwise described: halo is fluoro, chloro, bromo, or iodo. Alkyl, alkoxy, alkenyl, alkynyl, etc. denote both straight and branched groups; but reference to an individual radical such as "propyl" embraces only the straight chain radical, a branched chain isomer such as "isopropyl" being specifically referred to. Aryl denotes a phenyl radical or an ortho-fused bicyclic carbocyclic radical having about nine to ten ring atoms in which at least one ring is aromatic.

It will be appreciated by those skilled in the art that compounds of the invention having one or more chiral centers may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein. Preferably, the compound of formula (I) comprises the enantiomeric 8-azabicyclo[3.2.1] ring system corresponding to the 8-azabicyclo[3.2.1] ring system of (R)-cocaine or (−)-cocaine, wherein for a compound of formula (I), the carbon designated "a" has the (R) configuration and the carbon designated "b" has the (S) configuration. In formula (I), R$_1$ is in the β-position, as indicated by the wedged bond.

Specific and preferred values listed below for radicals, substituents, and ranges, are for illustration only; they do not exclude other defined values or other values within defined ranges for the radicals and substituents.

Specifically, (C$_1$–C$_4$)alkyl can be methyl, ethyl, propyl, isopropyl, butyl, iso-butyl, or sec-butyl; (C$_1$–C$_4$)alkoxy can be methoxy, ethoxy, propoxy, isopropoxy, butoxy, iso-butoxy, or sec-butoxy; (C$_2$–C$_4$)alkenyl can be vinyl, allyl, 1-propenyl, 2-propenyl, 1-butenyl, 2-butenyl, or 3-butenyl; (C$_2$–C$_4$)alkynyl can be ethynyl, 1-propynyl, 2-propynyl, 1-butynyl, 2-butynyl, or 3-butynyl; (C$_1$–C$_5$)alkanoyl can be acetyl, propanoyl, butanoyl, or pentanoyl; and aryl can be phenyl, indenyl, or naphthyl; aryl(C$_1$–C$_4$)alkyl can be benzyl or phenethyl; and arylcarbonyl can be benzoyl.

Specifically: R$_1$ can be hydrogen, OR$_7$, or N(R$_8$)$_2$; or R$_1$ can be OR$_7$, or N(R$_8$)$_2$; R$_3$ can be (C$_1$–C$_4$)alkyl, (C$_2$–C$_4$)alkenyl or (C$_2$–C$_4$)alkynyl; or R$_3$ can be (C$_2$–C$_4$)alkenyl or (C$_2$–C$_4$)alkynyl; and R$_7$ can be (C$_1$–C$_5$)alkanoyl, arylcarbonyl, or aryl (C$_1$–C$_5$)alkanoyl;.

A specific group of compounds are compounds of formula (I) wherein R$_1$ is hydrogen, aryl, (C$_1$–C$_4$)alkyl, OR$_7$, or N(R$_8$)$_2$; wherein any aryl in R$_1$ may optionally be substituted with 1, 2, or 3 substituents independently selected from the group consisting of halo (preferably I or Cl), CF$_3$, (C$_1$–C$_4$)alkoxy, (C$_1$–C$_4$)alkyl, (C$_1$–C$_4$)alkenyl, (C$_1$–C$_4$)alkynyl, amino, nitro and cyano; or a pharmaceutically acceptable salt thereof.

Another specific group of compounds are compounds of formula (I) wherein R$_1$ is aryl, aryl(C$_1$–C$_4$)alkyl, OR$_7$, or N(R$_8$)$_2$; or a pharmaceutically acceptable salt thereof.

Another specific group of compounds are compounds of formula (I) wherein R$_2$ is aryl or aryl(C$_1$–C$_4$)alkyl; wherein the aryl is substituted with 1, 2, or 3 substituents independently selected from the group consisting of halo (preferably I or Cl), CF$_3$, (C$_1$–C$_4$)alkoxy, (C$_1$–C$_4$)alkenyl, (C$_1$–C$_4$)alkynyl, amino, nitro and cyano; or a pharmaceutically acceptable salt thereof.

Another specific group of compounds are compounds of formula (I) wherein one of R$_4$ and R$_5$ is hydrogen, and the other is halo, CN, OR$_9$, COOR$_{10}$, arylSO$_2$—, or —CH$_2$NHR$_{11}$; or a pharmaceutically acceptable salt thereof.

A preferred compounds is compound 49, or compound 37; or a pharmaceutically acceptable salt thereof.

The present invention provides a method of synthesizing tropane analogs which makes it possible to prepare structures containing variable substituents at positions 2, 3, 4, 6 and 7 of the tropane skeleton. The present method can be used to synthesize structures previously found useful to exhibit useful activity in the treatment of Parkinson's disease. In addition, the present method may be used to synthesize novel tropane analogs. Efficient access to diverse cocaine analogs may also provide additional therapeutic agents, as well as providing means to manipulate the structure of cocaine to derive partial agonists for use in the discovery of anti-abuse therapies.

Tropane analogs of formula (I) can be synthesized as shown in FIGS. 1–7. The number following the named compounds refer to the numbered compounds. A pyridinium betaine-based dipolar cycloaddition route was used to obtain the tropenone of formula III, and this intermediate was transformed to products of formula I. Oxidopyridinium betaine was obtained as a crystalline, storable reagent, starting from the known 4-phenyl-3-hydroxypyridine 1 (FIG. 1)(Commins et al., *J. Heterocyvclic Chem.* 22:1419 (1985)). Pyridine 1 was treated with methyliodide, and the resulting hydroxypyridinium salt 2 was stirred with the ion exchange resin IRA 400 (OH) in methanol to afford the desired betaine 3.

The betaine 3 was investigated for its ability to undergo dipolar cycloaddition chemistry with 2 π addends. Using acrylonitrile as the test addend it was found that the 1,3-dipolar cycloaddition reaction proceeded readily when carried out at reflux temperatures for 3 hours. Two major adducts 4a and 4b were isolated. These compounds are of a single regiochemistry and of either 6β (4a, 38% isolated yield) or 6a (4b, 43%) stereochemistry. In addition, small amounts of the other two regioisomeric products were isolated (4c, 7β-isomer, 5% and 4d, 7a isomer, 17%, see FIG. 1 and Table 1). Similar results were achieved upon using phenyl vinylsulfone as the dipolarophile and acetonitrile as solvent. After 3 hours at reflux, the resulting mixture contained 5a as the major reaction product together with small amounts of the isomers 5b and 5c. In this particular case isomer 5d could not be detected (Table 1). The results achieved using methyl acrylate are also provided in the accompanying Table. NMR assignments of all of the pure isomers were made through the use of COSY, DEPT, and HETCOR experiments.

Table 1.

Products and isolated yields obtained for the reaction of betaine 3 with

| Compound Number* | X | Y | W | Z | Yield (%) |
|---|---|---|---|---|---|
| 4a | CN | H | H | H | 38 |
| 4b | H | CN | H | H | 43 |
| 4c | H | H | CN | H | 5 |
| 4d | H | H | H | CN | 17 |
| 5a | SO$_2$Ph | H | H | H | 60 |
| 5b | H | SO$_2$Ph | H | H | 16 |
| 5c | H | H | SO$_2$Ph | H | 15 |
| 5d | H | H | H | SO$_2$Ph | 0 |
| 6a | CO$_2$Et | H | H | H | 33 |
| 6b | H | CO$_2$Et | H | H | 20 |
| 6c | H | H | CO$_2$Et | H | 26 |
| 6d | H | H | H | CO$_2$Et | 12 |

*See FIG. 1 for structures of compound 4–6.

Figure 2:
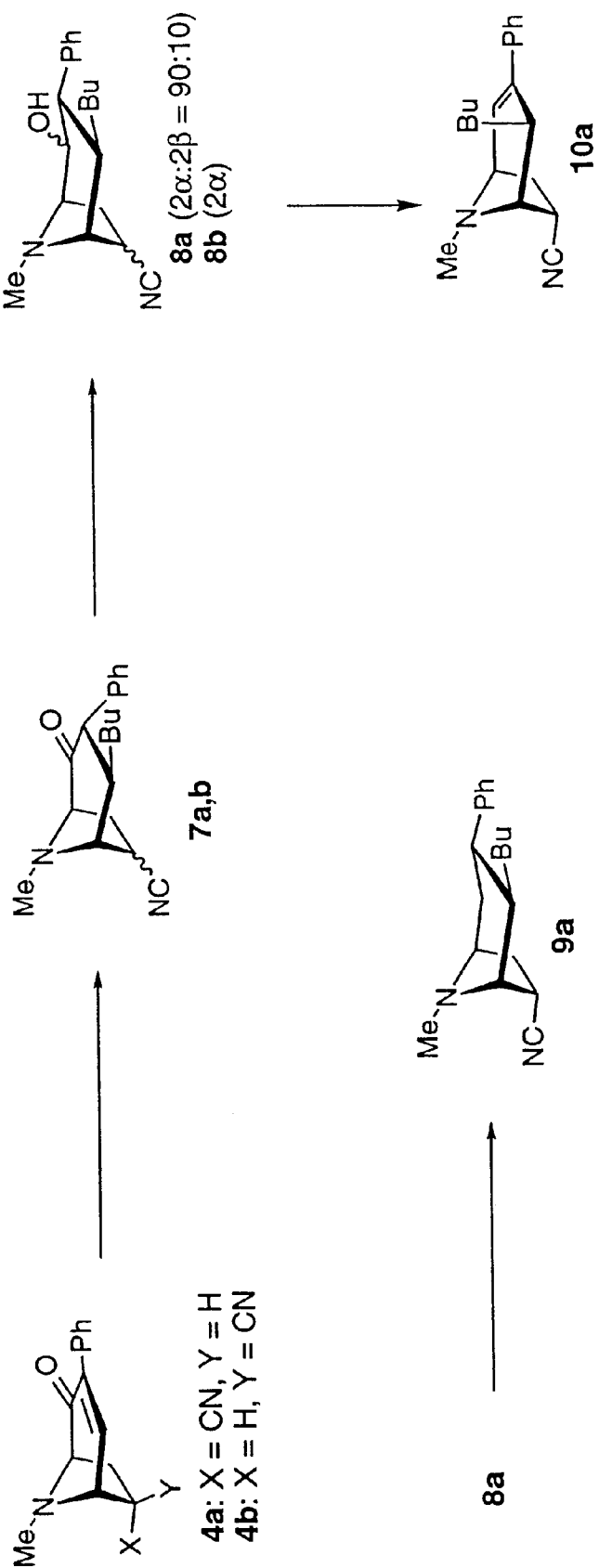
FIG. 2 illustrates the synthesis of certain compounds of formula (I).

To investigate the general utility of these tropenone intermediates to afford access to a wide variety of 3-phenyltropanes, further chemistry was carried out on 4a. For example, reaction of 4a with n-butylmagnesium bromide in the presence of cuprous bromide and trimethylsilyl chloride (Horiguchi et al., *Tetrehedron Lett.* 27(34):4025 (1986)) at −78° C. furnished the conjugate addition product 7a in 98% yield (FIG. 2). The ketone 7a was reduced in turn with sodium borohydride to afford predominantly the 2α alcohol 8a in 83% yield. Next, the alcohol was treated with phenyl thionochloroformate and n-BuLi in THF (Berkowitz et al., *J. Org. Chem.*, 61:4666 (1996)) at −78° C. to provide the thionocarbonate which was deoxygenated with Bu$_3$SnH to the tropane 9a. Alternatively, the alcohol 8a is dehydrated with the Burgess reagent (Burgess et al., *J. Org. Chem.*, 38:26 (1973)) to provide the olefin 10a. Subsequent hydrogenation provided a readily separable 6:4 mixture of 9a and 13a.

While the sequence of reactions shown in FIG. 2 provides ready access to a new series of tropane derivatives possessing substitution at the 6 and/or 7-positions, together with the α-stereochemistry of the phenyl substituent and consequently a boat conformation for the piperidine ring, efficient access was desired to those analogues possessing cocaine-like stereochemistry. Specifically, an alternate method was developed to transform the tropenone intermediate to the tropane having a chair-like conformation for its piperidine ring and with the substituents at positions 2 and 3 having β stereochemistry.

Figure 3:
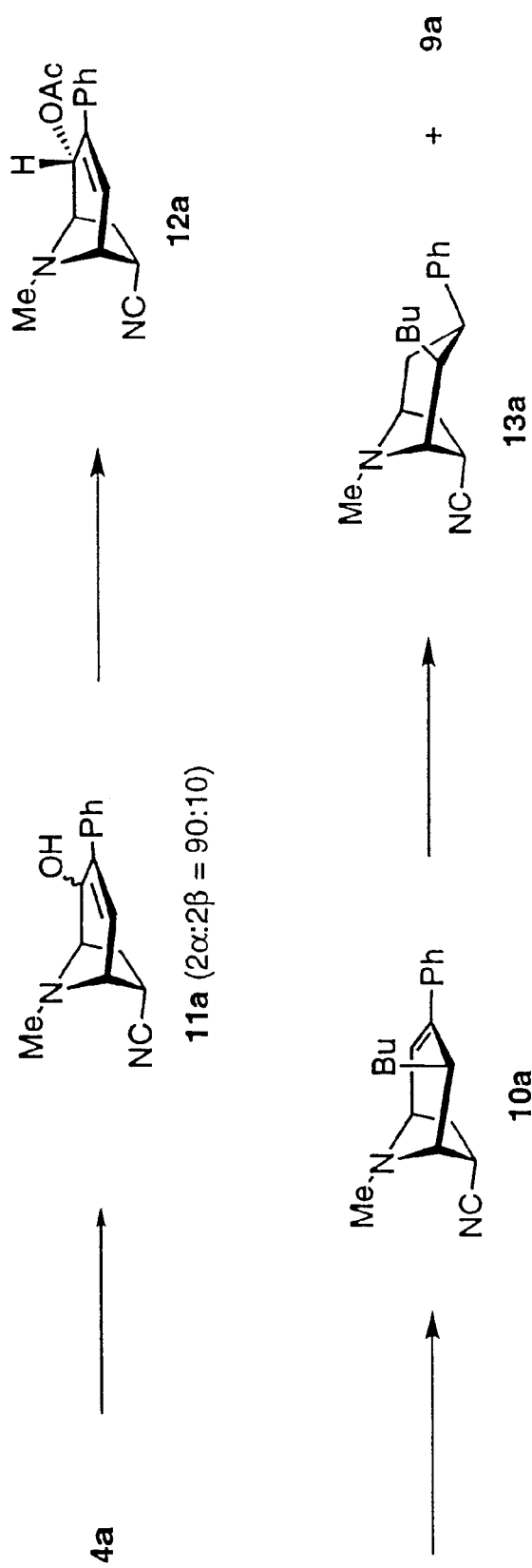
FIG. 3 illustrates an alternative method of synthesizing compounds of formula (I).
Figure 4:
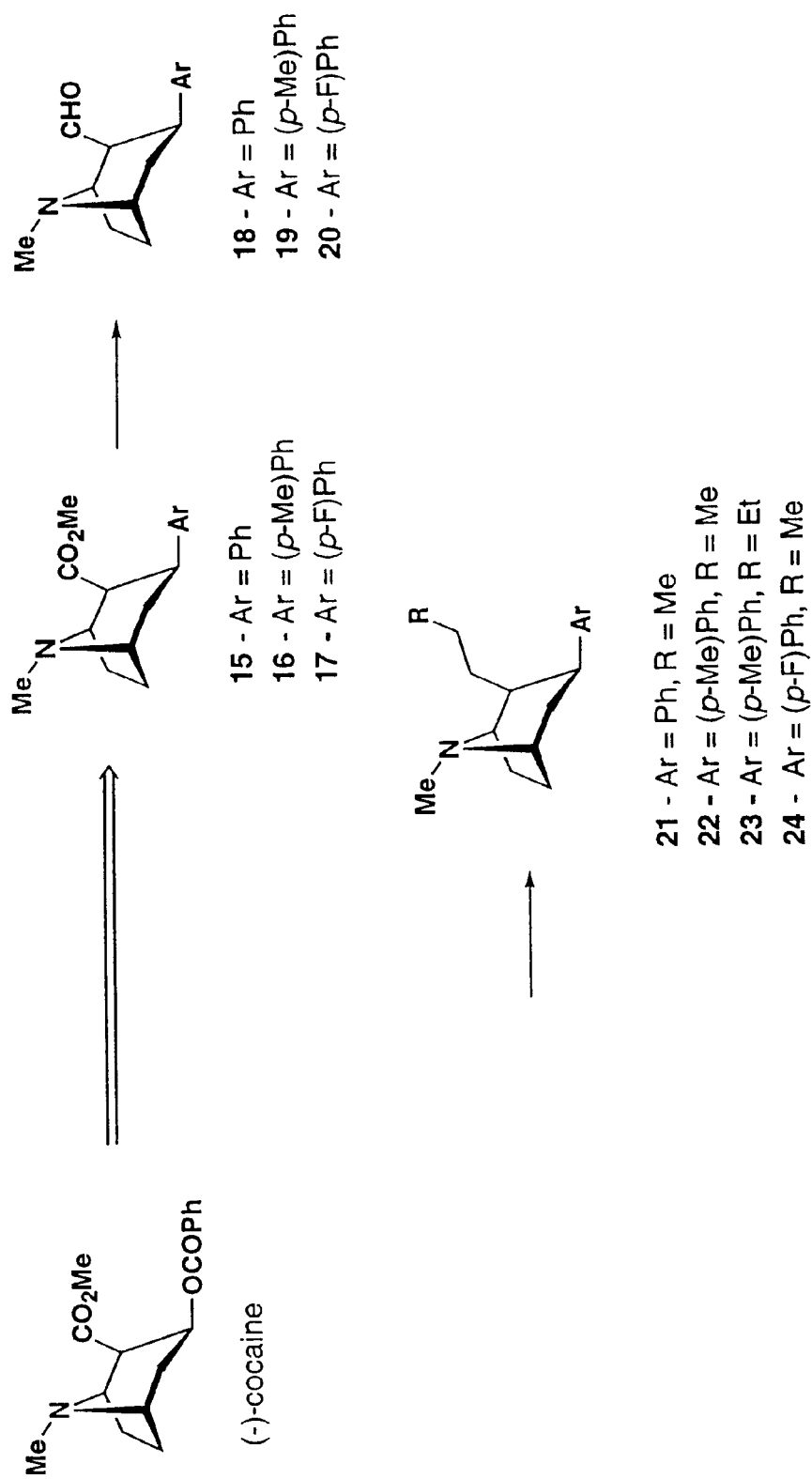
FIG. 4 illustrates the synthesis of certain compounds of formula (I) as prepared in Examples 8–11.
Figure 5:
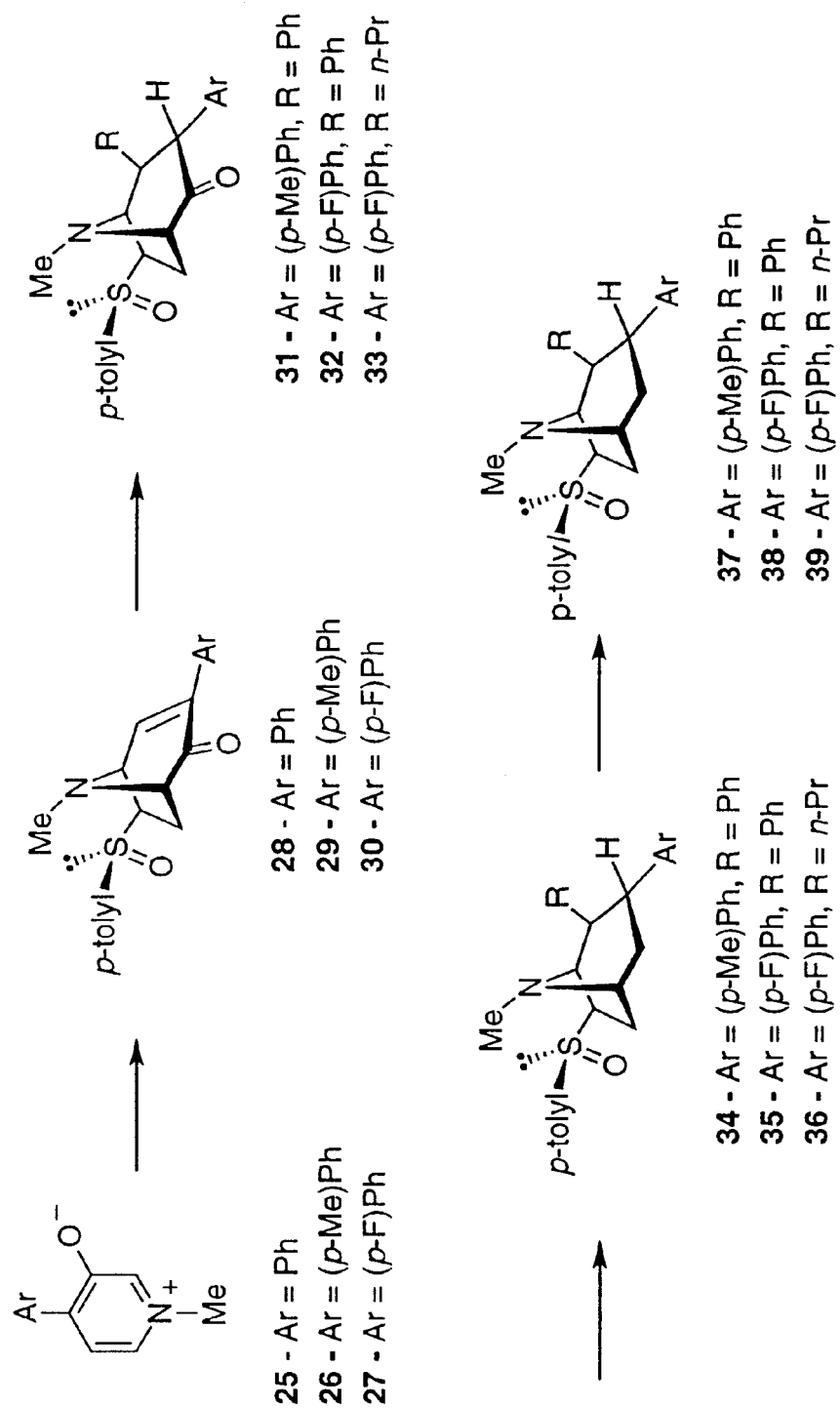
FIG. 5 illustrates the synthesis of certain compounds of formula (I) as prepared in Examples 12–14.
Figure 6:
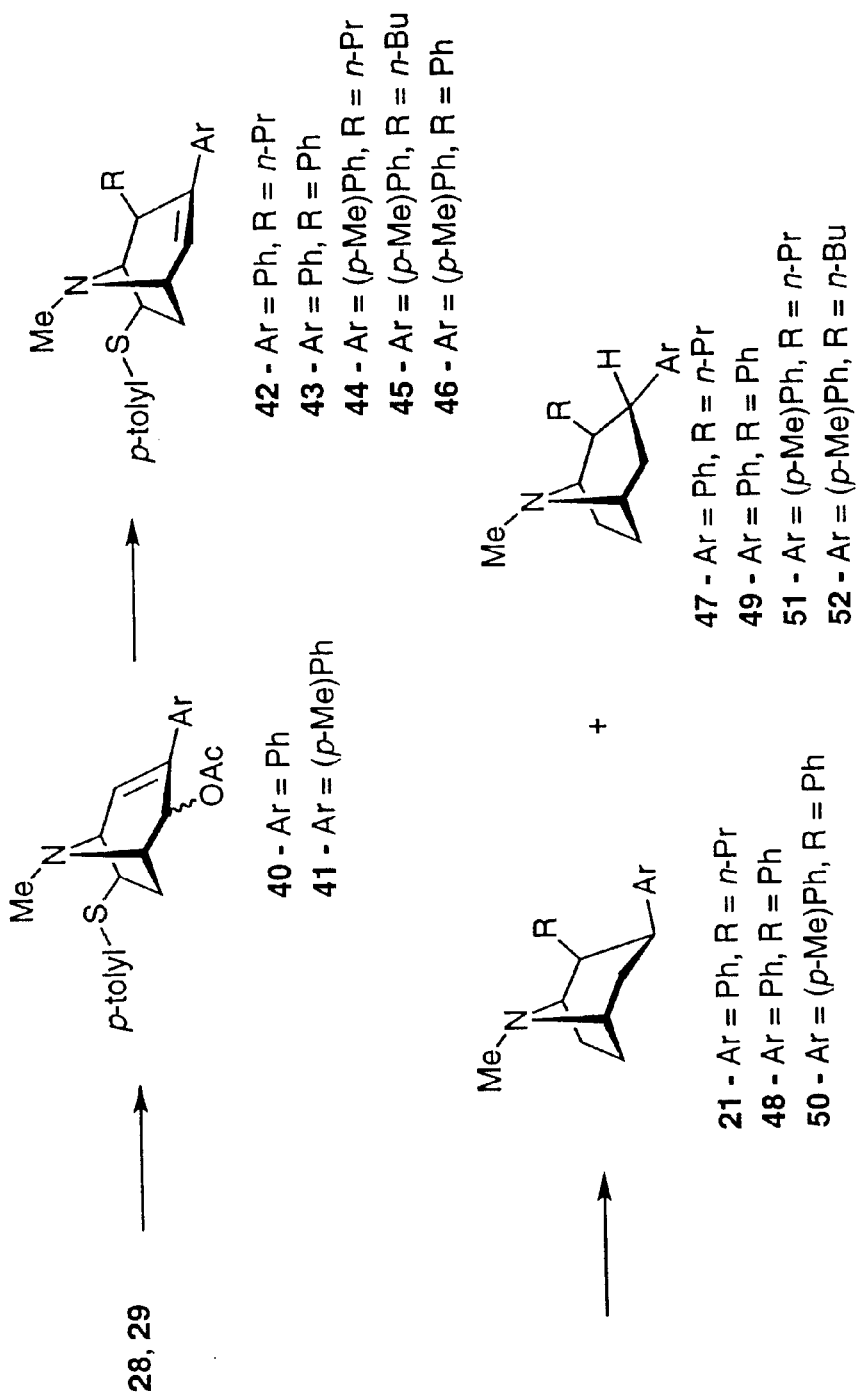
FIG. 6 illustrates the synthesis of certain compounds of formula (I) as prepared in Examples 15–21.
Figure 7:
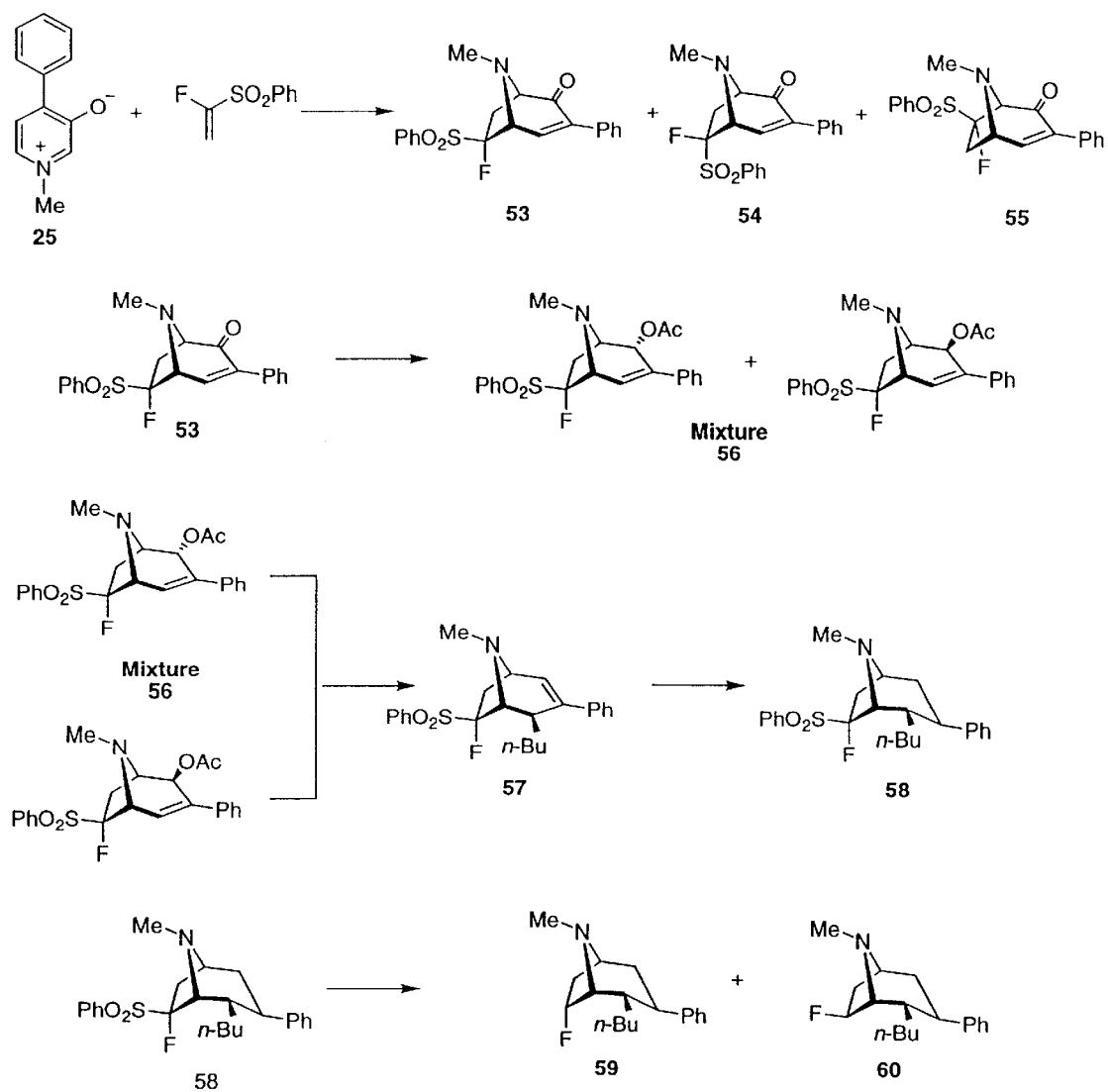
FIG. 7 illustrates the synthesis of certain compounds of formula (I) as prepared in Examples 5–6.

As shown in FIG. 3, the tropane derivatives of formula I may be obtained starting from the intermediate VI via the reduction of the ketone 4a to alcohol 11a using sodium borohydride/cerium chloride in methanol (Luche, *J. Am. Chem. Soc.*, 100:2226 (1978)). This alcohol was converted to its allylic acetate 12a with acetic anhydride and pyridine, and a cuprous cyanide catalyzed anti $S_N2'$ reaction (Tseng et al., *J. Org. Chem.* 51:2884 (1986)) was carried out using n-butylmagnesium bromide as nucleophile to afford the olefin 10a. This olefin was subjected in turn to hydrogenation (30 psi, MeOH) over palladium on carbon to yield the 2β,3β-isomer 13a together with the product 9a derived from β-face hydrogenation. This $S_N2'$ chemistry thus affords a higher yielding route to compound 13a than the dehydration method shown in FIG. 2.

The foregoing chemistry is expected to be applicable to a range of other tropenones derived from any of a number of other reactive dipolarophiles. The dipolar cycloaddition strategy can be used to create a stereodefined library of tropane structures for biological assay. The invention also provides the use of dipolarophiles bearing chiral auxiliary groups to permit access to optically pure tropanes as well as the attachment of the betaine to resin supports for use in combinatorial chemistry approaches.

A specific compound of formula I is a compound of formula XI:

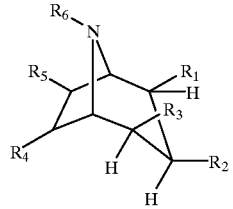

(XI)

wherein

R$_1$ is H, OR$_7$ where R$_7$ is H, (C$_1$–C$_4$)alkyl, (C$_1$–C$_4$)alkylC(O)—, (C$_5$–C$_7$)arylC(O)—; NHR$_8$ where R$_8$ is H, (C$_1$–C$_4$)alkyl, (C$_1$–C$_4$)alkylC(O)— or (C$_5$–C$_7$)arylC(O)—;

R$_2$ is phenyl or benzyl (preferably phenyl), each optionally substituted with halo (preferably I or Cl), CF$_3$, (C$_1$–C$_4$)alkoxy, (C$_1$–C$_4$)alkyl, (C$_1$–C$_4$)alkenyl, (C$_1$–C$_4$)alkynyl, amino, nitro or (C$_5$–C$_7$)aryl;

R$_3$ is (C$_1$–C$_4$)alkyl, (C$_1$–C$_4$)alkenyl or (C$_1$–C$_4$)alkynyl;

R$_4$ and R$_5$ are independently H, halo, CN, OR$_9$ where R$_9$ is H, (C$_1$–C$_4$)alkyl, (C$_1$–C$_4$)alkylC(O)—, (C$_5$–C$_7$)arylC(O)—; COOR$_{10}$ where R$_{10}$ is H or (C$_1$–C$_4$)alkyl; or CH$_2$NHR$_{11}$ where R$_{11}$ is H or (C$_1$–C$_4$)alkyl; and R$_6$ is H, (C$_1$–C$_4$)alkyl, (C$_1$–C$_4$)alkenyl, (C$_1$–C$_4$)alkynyl or benzyl (preferably (C$_1$–C$_4$)alkyl); or a stereoisomer thereof; or a pharmaceutically acceptable salt thereof.

One specific embodiment of the invention provides a method of synthesizing a compound of formula (XII):

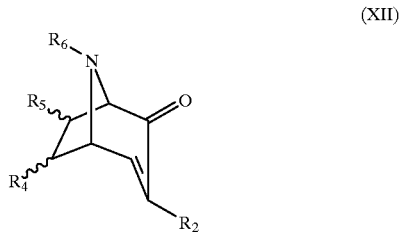

(XII)

wherein $R_2$ is phenyl or benzyl, optionally substituted with halo, $CF_3$, $(C_1-C_4)$alkoxy, $(C_1-C_4)$alkyl, $(C_1-C_4)$alkenyl, $(C_1-C_4)$alkynyl, amino, nitro or $(C_5-C_7)$aryl;

$R_4$ and $R_5$ are independently H, halo, CN, $OR_9$ where $R_9$ is H, $(C_1-C_4)$alkyl, $(C_1-C_4)$alkylC(O)—, $(C_5-C_7)$arylC(O)—; $COOR_{10}$ where $R_{10}$ is H or $(C_1-C_4)$alkyl; or $CH_2NHR_{11}$ where $R_{11}$ is H or $(C_1-C_4)$alkyl, provided that one of $R_4$ and $R_5$ is H; and $R_6$ is H, $(C_1-C_4)$alkyl, $(C_1-C_4)$alkenyl, $(C_1-C_4)$alkynyl or benzyl;

comprising the step of reacting a compound of formula (IV):

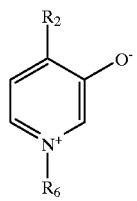

(IV)

with $CH_2=CH-R$, where R is halo, CN, $OR_9$, $COOR_{10}$, or $CH_2NHR_{11}$. Preferably, the reaction can be conducted with heating in a suitable organic solvent, i.e., under reflux conditions.

According to the invention, this specific embodiment may further comprise the step of reacting the compound of formula (XII) with $R_3$—MgBr, where $R_3$ is $(C_1-C_4)$alkyl, $(C_1-C_4)$alkenyl or $(C_1-C_4)$alkynyl; a source of Cu(I), and a hydroxy protecting reagent such as $((C_1-C_4)alkyl)_3SiCl$ followed by removal of the protecting group, to yield a compound of formula (XIII):

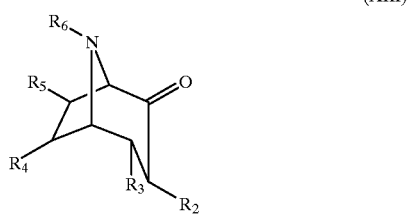

(XIII)

According to the invention, this specific embodiment may further comprises the steps of reducing the keto group in the compound of formula (XIII) to yield a compound of formula (XIV):

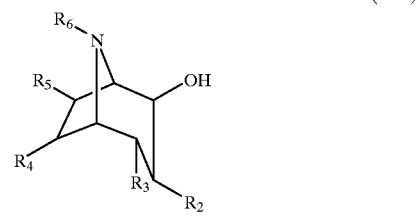

(XIV)

and reacting the compound of formula (XIV) with an anhydride of the formula $CH_3C(O)O—R_7$, where $R_7$ is $(C_1-C_4)$alkylC(O)— or $(C_5-C_7)$arylC(O)— to yield a compound of formula (XV):

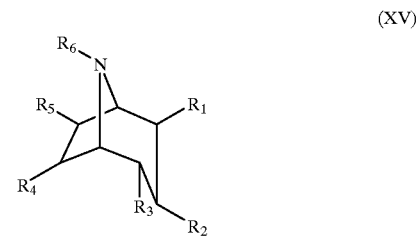

(XV)

where $R_1$ is $OR_7$.

In another specific embodiment the invention provides a method of synthesizing a compound of formula (XVI):

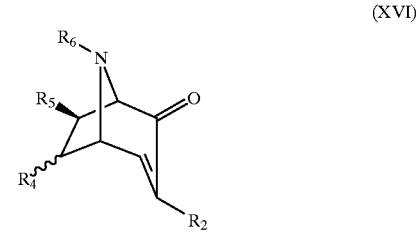

(XVI)

wherein $R_2$ is phenyl or benzyl, optionally substituted with halo, $CF_3$, $(C_1-C_4)$alkoxy, $(C_1-C_4)$alkyl, $(C_1-C_4)$alkenyl, $(C_1-C_4)$alkynyl, amino, nitro or $(C_5-C_7)$aryl;

$R_4$ and $R_5$ are H or $SO_2Ph$, provided that one of $R_4$ or $R_5$ is H and the other is $SO_2Ph$; and $R_6$ is H, $(C_1-C_4)$alkyl, $(C_1-C_4)$alkenyl, $(C_1-C_4)$alkynyl or benzyl;

comprising the steps of reacting a compound of formula (IV):

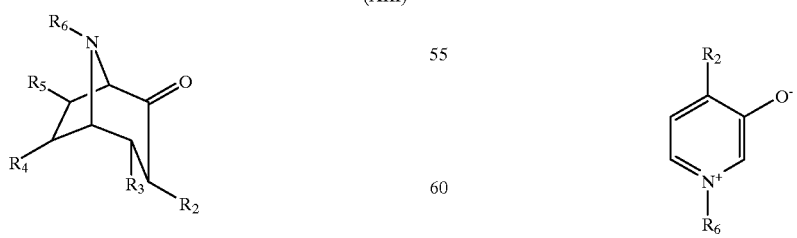

(IV)

with $CH_2=CH-SO_2Ph$.

In cases where compounds are sufficiently basic or acidic to form stable nontoxic acid or base salts, administration of the compounds as salts may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and α-glycerophosphate. Suitable acid addition salts of inorganic acids may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

The compounds of formula I can be formulated as pharmaceutical compositions and administered to a mammalian host, such as a human patient in a variety of forms adapted to the chosen route of administration, i.e., orally or parenterally, by intravenous, intramuscular, topical or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and.the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form must be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful dosages of the compounds of formula I can be determined by comparing their in vitro activity, and in vivo activity in animal models. Methods for the extrapolation of effective dosages in mice, and other animals, to humans are known to the art; for example, see U.S. Pat. No. 4,938,949.

Generally, the concentration of the compound(s) of formula I in a liquid composition, such as a lotion, will be from about 0.1–25 wt-%, preferably from about 0.5–10 wt-%. The concentration in a semi-solid or solid composition such as a gel or a powder will be about 0.1–5 wt-%, preferably about 0.5–2.5 wt-%. Single dosages for injection, infusion or ingestion will generally vary between 50–1500 mg, and may be administered, i.e., 1–3 times daily, to yield levels of about 0.5–50 mg/kg, for adults.

Accordingly, the invention includes a pharmaceutical composition comprising a compound of formula I as described hereinabove; or a pharmaceutically acceptable salt thereof; in combination with a pharmaceutically acceptable carrier.

Figure 8:
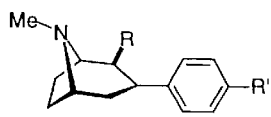
FIG. 8 shows biological data for representative compounds of formula (I).

The ability of representative compounds of the invention to displace [$^3$H]mazindol was determined using TestA below. [$^3$H]Mazindol has been shown to label the cocaine binding sites on the dopamine transporter of rat striatal membranes (Kozikowski et al. *Med. Chem. Res.,* 1991, 312–321), and it binds with high affinity to a single, sodium-dependent site in striatal membranes representing the dopamine carrier. Additionally, the ability of representative compounds of the invention to inhibit high-affinity uptake of [³H]dopamine and [3H]serotonin into striatal nerve endings (synaptosomes) was determined using known protocols (see M. C. Ritz et al. *Science,* 1988, 1219; and by M. J. Kuhar et al. *Life Sci.,* 1973, 13, 1623–1634), as described in Test B below. Results from Test A and Test B are presented in FIG. 8.

Test A

[³H]Mazindol Binding Assay

Caudate nuclei were homogenized in buffer consisting of 5 mM HEPES, 5 mM KCl and 100 mM NaCl (pH 7.4) and centrifuged for 10 min at 39,000×g. The pellet was resuspended in buffer and centrifuged again. Finally, the pellet was resuspended in 30 volumes of buffer, pelleted at 15,000×g and frozen at −80° C. until used. The striatal homogenates were thawed by resuspension in the buffer described above at 75–125 µg protein/ml and incubated with [³H]mazindol, with or without competing drugs, for 60 min in a 4° C. cold room. Non-specific binding was determined with 30 µM cocaine. The bound and free [³H]mazindol was separated by rapid vacuum filtration over Whatman GF/C filters, using a Brandel M24R cell harvester, followed by two washes with 5 ml of cold buffer. Radioactivity on the filters was then extracted by vortexing with 5 ml of scintillant and the vials counted. $IC_{50}$ values were determined using the computer program LIGAND.

Test B

Uptake of [³H]dopamine and [³H]serotonin was carried out using synaptosomes from the same brain regions as described above for binding assays. A Krebs phosphate buffer, pH 7.4, containing 1 µM pargyline, dextrose (1.9 mg/ml), and ascorbic acid (0.2 mg/ml) was used. Synaptosomes were prepared by homogenizing fresh tissue in 20 volumes of ice-cold 0.32 M sucrose using a glass-teflon homogenizer. Nuclei and large tissue fragments were removed by centrifugation at 800×g for 10 minutes. The supernatant was centrifuged at 20,000×g for 15 minutes to collect synaptosomes in a pellet. The pellet was resuspended in 0.32 M sucrose at a concentration of 15, 100 or 10 mg/ml original wet weight, and diluted 10 fold in the assay tubes. The final assay volume was 1.0 ml and the duration of incubation at 30° C. was 3 minutes so that uptake was inear with time in contrast to binding assays where binding had reached equilibrium.

$K_i$ values were determined using serial dilutions of the analogues. A thirty minute preincubation of the analogues with the tissue was utilized before uptake was initiated by adding tritiated substrate. The preincubation was utilized to allow analogue and transporters to reach an equilibrium so that kinetic effects were not a significant factor. $K_i$ values were determined using standard techniques.

Generally, compounds of the invention can bind to the cocaine recognition sight. Thus, the present compounds may be useful to treat drug addiction and in particular, cocaine addiction. Accordingly, the invention includes a method for the treatment of drug addiction in a human comprising administering to a human in need of such treatment a pharmaceutically effective dose of at least one compound of formula I; or a pharmaceutically acceptable salt thereof. Additionally, the invention provides a therapeutic method comprising inducing analgesia or vasoconstriction in a mammal, such as a human, by administering an effective amount of a compound of formula I, or a pharmaceutically acceptable salt thereof.

Compounds of the invention have also been shown to inhibit dopamine and/or serotonin uptake, and may be useful to treat diseases or conditions wherein the modulation of dopamine or serotonin uptake is desirable. Accordingly, the invention includes a method for treating a disease or condition in a human, in which the activity of dopamine or serotonin has been implicated and modulation of dopamine or serotonin uptake is desired comprising administering to a human in need of such treatment, a pharmaceutically effective dose of at least one compound of formula I; or a pharmaceutically acceptable salt thereof. The present compounds may be particularly useful to treat depression, obesity or Parkinson's disease.

Compounds of the invention may also be useful as imaging agents when labeled with a radionuclide. The radionuclide (such as tritium, iodine-125, iodine-131, iodine-123, astatine-210, carbon-11, carbon-14, nitrogen-13, fluorine-18) may be incorporated into, or attached directly to the core structure, as by halogenation; or the radionuclide (such as Tc-99m, Re-186) may be attached to a linking group or bound by a chelating group which is then attached to the compound of formula I directly, or by means of a linker. Radiolabeling techniques such as these are routinely used in radiopharmaceutical chemistry (see for example J. L. Neumeyer et al. *J. Med. Chein.* 1994, 37, 1558–1561 and J. L. Nuemeyer et al. *J. Med. Chem.* 1996, 39, 543–548). Accordingly, the invention also provides a radiolabeled compound comprising a radionuclide bound to a compound of formula I; or a pharmaceutically acceptable salt thereof, as well as a method of using such a radiolabeled compound as an imaging agent.

The 2β,3α diaryl derivatives, compounds 49 and 37, are highly selective for the dopamine transporter relative to the serotonin transporter. Due to this selectivity, radiolabeled compound comprising compound 49 or 37 may be particularly useful as imaging agents.

The invention also provides a method of imaging the brain of a mammal (i.e. a human) comprising administering to said mammal, a detectable amount of a radiolabeled compound, comprising radionuclide bound to a compound of formula (I), or a pharmaceutically acceptable salt thereof; and subsequently detecting the presence of said radiolabeled compound.

The invention also provides a compound of formula I for use in medical therapy (preferably for use in inducing analgesia or vasoconstriction in a mammal, or for use in treating cocaine abuse, depression, obesity, or Parkinson's disease), as well as the use of a compound of formula I for the manufacture of a medicament for inducing analgesia or vasoconstriction in a mammal, or for treating cocaine abuse, depression, obesity, or Parkinson's disease in a mammal, such as a human.

The invention also provides a radiolabeled compound comprising a radionuclide bound to a compound of formula I for use in medical imaging, as well as the use of a radiolabeled compound comprising a radionuclide bound to a compound of formula I, for the manufacture of a medicament useful for medical imaging.

The invention will be further described by reference to the following non-limiting examples wherein, unless otherwise noted:

a. Starting materials were obtained from Aldrich Chemicals or from other commercial suppliers;

b. Diethyl ether was purified by distillation from phosphorous pentoxide;

c. THF was freshly distilled under nitrogen from sodium-benzophenone;

d. IR spectra was recorded on an ATI Mattson spectrophotometer;
e. $^1$H and NMR spectra were obtained with a Varian Unity Inova at 300 and 75.46 MHz respectively. $^1$H chemical shifts (δ) are reported in ppm downfield from internal TMS;
f. $^{13}$C chemical shifts are referred to: CDCl$_3$ (central peak, δ=77.0 ppm), benzene-d$_6$ (central peak, δ=128.0 ppm) or DMSO-d$_6$ (central peak, δ=39.7 ppm);
g. NMR assignments were made with COSY, DEPT and HETCOR programs;
h. The subscript numbers are used to identify the protons in the tropane rings according to the following numbering scheme:

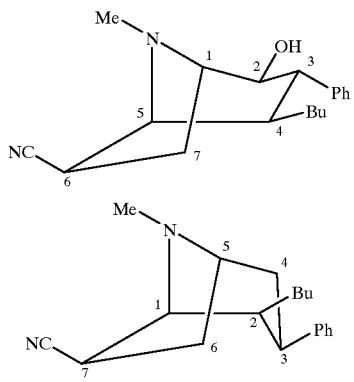

i. Melting points were determined in Pyrex capillaries with a Thomas Hoover Unimelt apparatus and are uncorrect;
j. MS were measured in the EI mode with an ionization potential of 70 eV;
k. TLC were performed on Merck glass silica gel plates;
l. column chromatography was performed using Merck silica gel 60 (60–200 mesh); and
m. The following abbreviations are used: DMSO as dimethyl sulfoxide, ether as diethyl ether; THF as tetrahydrofuran; EtOAc as ethyl acetate; DCM as dichloromethane; MeOH as methanol; EtOH as ethanol; CDCl$_3$ as chloroform-d$_1$.

EXAMPLES

Example 1
4β-Butyl-2-hydroxy-8-methyl-3α-phenyl-8-azabicyclo [3.2.1]octane-6-exo-carbonitrile (8a)

To a solution of 7a (0.55 g, 1.86 mmol) in EtOH (20 mL) was added portionwise NaBH$_4$ (0.21 g, 5.57 mmol). The resulting solution was stirred at 25° C. for 1 h then concentrated and the residue diluted with water (60 mL) and extracted with EtOAc (2×50 mL). The collected organic phase was washed with brine (80 mL), dried and concentrated under reduced pressure. The crude mixture containing the two hydroxy isomers was purified by flash chromatography on silica gel using EtOAc/n-hexane as eluant. 2α-hydroxy derivative (0.45 g, 81%): white solid; R$_f$=0.8 (EtOAc/n-hexane 1/1); $^1$H NMR (benzene-d$_6$) δ0.633 (d, OH, J$_{OH-2}$=3.0 Hz,), 0.721 (t, 3H, J=6.9 Hz), 0.9–1.15 (m, 5H), 1.16–1.30 (m, 1H), 1.358 (dt, H$_4$, J$_{4-3}$=11.1 Hz, J$_{4-1'}$=J$_{4-1''}$=6.0 Hz), 1.837 (dt, H$_{7ex}$, J$_{7ex-1}$=J$_{7ex-6}$=36.5 Hz, J$_{7ex-7en}$=11.1 Hz), 2.270 (s, 3H), 2.373 (dd, H$_6$, J$_{6-7en}$=9.0 Hz, J$_{6-7ex}$=7.1 Hz), 2.693 (dd, H$_{7en}$, J$_{7en-7ex}$=12.9 Hz, J$_{7en-6}$=9.6 Hz), 2.744 (dd, H$_3$, J$_{3-2}$=4.5 Hz, J$_{3-4}$=11.4 Hz), 3.105 (dd, H$_1$, J$_{1-2}$=8.4 Hz, J$_{1-7ex}$=6.9 Hz), 3.286 (s, H$_5$), 3.695(qd, H$_2$, J$_{2-OH}$=3.0 Hz, J$_{2-1}$=8.6 Hz, J$_{2-3}$=4.8 Hz), 6.85–6.98 (m, 2H), 7.0–7.1 (m, 3H); $^{13}$C NMR (benzene-d$_6$) δ14.10, 22.99, 26.73, 28.89, 34.40, 34.56, 42.03, 45.47, 47.19, 66.08, 70.57, 71.91, 123.95, 127.00, 128.89, 129.80, 140.40; Ms, m/z (%): 298 (M$^+$, 16), 255 (34), 245 (10), 177 (39), 135 (30), 107 (71), 42 (100); IR (film) 3466, 2932, 2231, 1451 cm$^{-1}$. 2β-hydroxy derivative (0.05 g, 9%): colorless oil; R$_f$=0.6 (EtOAc/n-hexane 1/1); $^1$H NMR (CDCl$_3$) δ 0.74 (t, 3H, J=7.2 Hz), 0.7–0.95 (m, 1H), 1.0–1.35 (m, 4H), 1.37–1.7 (m, 3H), 2.38 (dd, H$_{7endo}$, J$_{7en-6}$=6.0 Hz, J$_{7en-7ex}$=12.6 Hz), 2.44–2.60 (m, H$_3$ and H$_{7exo}$), 2.59 (s, 3H), 2.89 (dd, H$_6$, J$_{6-7en}$=6.0 Hz, J$_{6-7ex}$=9.6 Hz), 3.46 (bt, H$_1$, J=4.8 Hz), 3.63 (s, H$_5$), 4.27 (dd, H$_2$, J=3.0 Hz, J=10.5), 7.1–7.4 (m, 5H); $^{13}$C NMR (CDCl$_3$) δ13.93, 22.53, 27.57, 27.86, 29.75, 30.49, 42.56, 46.45, 46.67, 67.78, 68.65, 70.82, 124.03, 127.02, 128.61, 128.82, 138.12; Ms, m/z (%): 298 (M$^+$, 14), 255 (43), 245 (4), 241 (52), 177 (12), 135 (27), 107 (24), 42 (100);

The intermediate 7a was prepared as follows.
a. 1-Methyl-4-phenyl-3-hydroxypyridinium Iodide (2)

To a solution of 1 (4.1 g, 24.0 mmol) in acetone (100 mL) was added iodomethane (3.0 mL, 48.0 mmol). The mixture was refluxed for 3 h and stirred at 25° C. for 40 h then ether (100 mL) was added and the precipitated filtered off and washed with ether to afford compound 2 (6.8 g, 90%) as a pale yellow solid: mp 175° C.; $^1$H NMR (DMSO-d$_6$) δ4.31 (s, 3H), 7.53–7.61 (m, 3H), 7.76–7.84 (m, 2H), 8.07 (d, 1H, J=6.0 Hz), 8.35 (s, 1H), 8.528 (d, 1H, d, J=6.0 Hz), 12.1 (bs, 1H); $^{13}$C NMR (DMSO-d$_6$) δ47.46, 127.40, 128.81, 129.42, 130.20, 133.34, 133.55, 135.24, 142.27, 155.00.

b. 1-Methyl-4-phenyl-3-hydroxypyridine (3)
A mixture of 2 (4.03 g, 12.9 mmol) and IRA-OH (400) resin (20 mL) in MeOH was stirred at 25° C. for 1 h then the basic resin was filtered off and washed several time with MeOH. The resulting clear solution was concentrated under reduced pressure to afford the compound 3 (2.21 g, 92%) as a pale yellow solid used in the next step without further purification: mp 154–157° C.; $^1$H NMR (DMSO-d$_6$) δ3.97 (s, 3H), 7.3–7.52 (m, 5H), 7.38 (d, 1H, J=7.5 Hz), 8.04 (d, 1H, J=8.1 Hz), 8.053 (s, 1H).

c. 8-Methyl-2-oxo-3-phenyl-8-azabicyclo[3.2.1]oct-3-ene-6-carbonitrile and 8-methyl-2-oxo-3-phenyl-8-azabicyclo [3.2.1]oct-3-ene-7-carbonitrile (4a–d)

To a solution of 3 (2.21 g, 11.9 mmol) in acrylonitrile (20 mL) was added a small amount of hydroquinone and the mixture refluxed under nitrogen for 1 h then concentrated under reduced pressure. The four isomers 4a–d present in the crude mixture were separated by flash chromatography on silica gel using EtOAc/n-hexane as eluant. 4a (1.07 g, 37%): pale yellow solid; mp 129–130° C.; R$_f$=0.6 (EtOAc/n-hexane 4/6); $^1$H NMR (CDCl$_3$) δ2.19 (dd, H$_{7endo}$, J$_{7en-7ex}$=12.8 Hz, J$_{7en-6}$=9.3 Hz), 2.617 (s, 3H), 2.78 (qd, H$_{7exo}$, J$_{7ex-6}$=3.3 Hz, J$_{7ex-1}$=7.5 Hz, J$_{7ex-7en}$=13.8 Hz), 3.064 (dd, H$_6$, J$_{6-7ex}$=3.6 Hz, J$_{6-7en}$=90 Hz), 3.837 (d, H$_1$, J$_{1-7ex}$=7.5 Hz), 4.183 (d, H$_5$, J$_{5-4}$=5.4 Hz), 6.967 (d, H$_4$, J$_{4-5}$=5.4 Hz), 7.36 (bs, 5H); $^{13}$C NMR (CDCl$_3$) δ30.37, 31.63, 36.03, 64.72, 70.16, 121.34, 128.15, 128.29, 128.69, 133.08, 138.771, 141.12, 196.40. 4b (1.23 g, 42%): pale yellow solid; mp 110–112° C.; R$_f$=0.42 (EtOAc/n-hexane 8/2); $^1$H NMR (CDCl$_3$) δ2.00 (dd, H$_{7endo}$, J$_{7en-7-ex}$=13.8 Hz, J$_{7en-6}$=5.7 Hz), 2.47 (s, 3H), 2.88 (qd, H$_{7exo}$, J$_{7ex-6}$=10.2 Hz, J$_{7ex-7en}$=13.8 Hz, J$_{7ex-1}$=7.8 Hz), 3.446 (dt, H$_6$, J$_{6-5}$=J$_{6-7en}$=5.4 Hz, J$_{6-7ex}$=11.4 Hz), 3.75 (d, H$_1$, J$_{1-7ex}$=7.5 Hz), 4.184 (t,H$_5$, J$_{5-4}$=J$_{5-6}$=5.4 Hz), 7.141 (d, H$_4$, J$_{4-5}$=5.4 Hz), 7.3–7.5 (m, 5); $^{13}$C NMR (CDCl$_3$) δ29.93, 30.72, 36.83, 62.45, 70.67, 119.623, 128.26, 128.46, 128.66, 133.33, 139.84, 142.08, 195.99. 4c (0.15 g, 5%): pale yellow wax; $R_f$=0.4 (EtOAc/n-hexane 4/6); $^1$H NMR (benzene-d$_6$) δ1.222 (dd, H$_{6endo}$, J$_{6en-6ex}$=12.3 Hz, J$_{6en-7}$=9.3 Hz), 1.842 (dt, H$_{6exo}$, J$_{6ex-5}$=J$_{6ex-7}$=6.3 Hz, J$_{6ex-6en}$=12.3 Hz), 1.956 (s, 3H), 1.9–2.0 (m, H$_7$), 2.879 (dd, H$_5$, J$_{5-4}$=5.4Hz, J$_{5-6ex}$=6.0 Hz), 3.75 (s, H$_1$), 6.12 (d, H$_4$, J$_{4-5}$=5.4Hz), 7.1–7.2 (m, 3H), 7.3–7.4 (m, 2H); $^{13}$C NMR (benzene-d$_6$) δ27.91, 34.56, 37.12, 61.42, 76.07, 116.64, 121.55, 128.91, 128.936, 134.56, 137.05, 146.20, 193.19. 4d (0.47 g, 16%): pale yellow solid; mp 117° C., $R_f$=0.26 (EtOAc/n-hexane 8/2); $^1$H NMR (benzene-d$_6$) δ1.417 (dd, H$_{6endo}$, J$_{6en-7}$=3.3 Hz, J$_{6en-6ex}$=12.3 Hz), 1.64 (qd, H$_{6exo}$, J$_{6ex-6en}$=12.3 Hz, J$_{6ex-7}$=10.5 Hz, J$_{6x-5}$=5.7 Hz), 1.746 (s, 3H), 2.518 (qd, H$_7$, J$_{7-1}$=7.2 Hz, J$_{7-6ex}$=10.8 Hz, J$_{7-6ex}$=3.3 Hz), 2.807 (t, H$_{5-4}$=J$_{5-6ex}$=5.7 Hz), 3.44 (d, H$_1$, J$_{1-7}$=7.5 Hz), 6.28 (d, H$_4$, J$_{4-5}$=5.4 Hz), 7.05–7.20 (m, 3H), 7.43–7.58 (m, 2H); $^{13}$C NMR (benzene-d$_6$) δ26.04, 33.91, 37.31, 61.35, 73.43, 119.12, 128.29, 128.30, 128.53, 133.59, 138.43, 146.08, 193.57.

d. 4β-Butyl-8-methyl-2-oxo-3α-phenyl-8-azabicyclo[3.2.1] octane-6-exo-carbonitrile (7a)

To a cooled (−78° C.) mixture of n-butylmagnesium bromide (1.05 mL, 1.01 mmol, 0.96 M in ether), HMPA (0.35 mL, 2.01 mmol) and CuBr.Me$_2$S (8.6 mg, 0.04 mmol) was added dropwise a mixture of 4a (200 mg, 0.84 mmol) and trimethylsilyl chloride (0.21 mL, 1.68 mmol) in dry THF (10 mL). After 1 h the reaction was quenched with a 20% solution of NH$_4$OH (20 mnL) and extracted with EtOAc (30 mL). The organic phase was washed with brine (30 mL), dried and concentrated under reduced pressure. The crude mixture containing the silyl enol ether intermediate was diluted with MeOH (5 mL) and potassium fluoride was added (24 mg, 0.84 mmol). The resulting solution was stirred at 25° C. for 5 min then concentrated under reduced pressure and the crude mixture purified by flash chromatography on silica gel using EtOAc/n-hexane as eluant to afford the title compound (220 mg, 88%) as a wax: $R_f$=0.8 (EtOAc/n-hexane 1/1); $^1$H NMR (CD$_3$OD) δ0.82 (t, 3H, J=7.2 Hz), 1.1–1.35 (m, 3H), 1.37–1.5 (m, 4H), 1.5–1.7 (m, H$_4$), 2.314 (dd, H$_{7en}$, J$_{7en-7ex}$=13.5 Hz, J$_{7en-6}$=9.9 Hz), 2.573 (s, 3H), 2.66 (dt, H$_{7ex}$, J$_{7ex-7en}$=13.8 Hz, J$_{7ex-6}$=J$_{7ex-1}$=7.2 Hz), 3.06 (dd, H$_6$, J$_{7ex}$=6.9 Hz, J$_{6-7en}$=9.6 Hz), 3.55 (d,H$_3$, J$_{3-4}$=8.7 Hz), 3.674 (s, H$_5$), 3.76 (d, H$_1$, J$_{1-7ex}$=7.2 Hz), 6.95–7.10 (m, 2H), 7.2–7.4 (m, 3H); $^{13}$C NMR (benzene-d$_6$) δ14.35, 23.25, 29.16, 33.47, 33.50, 34.73, 40.74, 48.82, 56.82, 72.53, 73.08, 123.03, 127.64, 128.90, 130.42, 131.24, 138.19, 209.46; IR (film) 2955, 2234, 1723, 1453 cm$^{-1}$.

Example 2

4β-Butyl-2α-hydroxy-8-methyl-3α-phenyl-8-azabicyclo[3.2.1]octane-6-endo-carbonitrile (8b)

Using a procedure similar to that described in Example 1, except replacing the compound 7a used therein with compound 7b, the title compound was obtained (95%) as a white solid: $R_f$=0.4 (EtOAc/n-hexane 1/1); $^1$H NMR (benzene-d$_6$) δ0.797 (t, 3H, J=7.2 Hz), 0.903 (bs, OH), 1.0–1.4 (m, 6H), 1.631 (qd, H$_{7ex}$, J$_{7ex-6}$=12 Hz, J$_{7ex-7en}$=13.5 Hz, J$_{7ex-1}$=7.5 Hz), 1.735 (s, 3H), 2.387 (dd, H$_4$, J$_{4-3}$=11.4 Hz, J$_{4-1'}$=9.6 Hz), 2.538 (dt, H$_6$, J$_{6-5}$=J$_{6-7en}$=6.3 Hz, J$_{6-7ex}$=12.0 Hz), 2.757 (dd, H$_{7en}$, J$_{7en-7ex}$=13.5 Hz, J$_{7en-6}$=6.3 Hz), 2.813 (d, H$_5$, J$_{5-6}$=6.0 Hz), 2.90 (dd, H$_3$, J$_{3-2}$=5.4 Hz, J$_{3-4}$=12.0 Hz), 2.972 (dd, H$_1$, J$_{1-2}$=8.2 Hz, J$_{1-7}$, =7.3 Hz), 3.892 (qd, H$_2$, J$_{2-OH}$=2.1 Hz, J$_{2-1'}$, =8.1 Hz, J$_{2-3}$=5.1 Hz), 6.98–7.20 (m, 5H); $^{13}$C NMR (benzene-d$_6$) δ14.16, 22.98, 24.553, 28.59, 30.05, 34.56, 38.68, 41.02, 47.37, 65.31, 68.27, 70.15, 121.73, 126.97, 128.92, 130.19, 139.78; MS, m/z (%): 298 (M$^+$, 14), 255 (30), 241 (8), 177 (10), 137 (29), 82 (52), 42 (100).

The intermediate compound 7b was prepared as follows.

a. 4β-Butyl-8-methyl-2-oxo-3α-phenyl-8-azabicyclo[3.2.1] octane-6-endo-carbonitrile (7b)

Using a procedure similar to that described in Example 1, sub-part f, except replacing the compound 4a used therein with compound 4b, compound 7b was prepared (95%) as a colorless oil: $R_f$=0.6 (EtOAc/n-hexane); $^1$H NMR (benzene-d$_6$) δ0.721 (t, 3H, J=6.9 Hz), 1.0–1.43 (m, 6H), 1.522 (s, 3H), 1.68–1.88 (m, H$_{7endo}$ and H$_{7exo}$), 2.227 (td, H$_4$, J$_{4-3}$=J$_{4-1'}$=9.3 Hz, J$_{4-1'}$=3.0 Hz), 2.347 (dt, H$_6$, J$_{6-5}$=J$_{6-7en}$=6.3 Hz, $_{6-7ex}$=11.7 Hz), 2.85 (d, H$_5$, J$_{5-6}$=6.3 Hz), 2.967 (d, H$_1$, J$_{1-7en}$=7.2 Hz), 3.442 (d, H$_3$, J$_{3-4}$=9.6 Hz), 7.0–7.2 (m, 5H); $^{13}$C NMR (CDCl$_3$) δ13.86, 22.41, 28.66, 29.44, 32.084, 33.95, 40.16, 40.54, 56.06, 68.30, 71.65, 120.29, 127.25, 128.58, 129.74, 136.78, 210.82; IR (film) 2956, 2930, 2235, 1724, 1462, 1105 cm$^{-1}$.

Example 3

2β-Butyl-8-methyl-3α-phenyl-8-azabicyclo[3.2.1]octane-6-exo-carbonitrile (9a)

A solution of 14a (20 mg, 0.046 mmol), Bu$_3$SnH (0.02 mL, 0.069 mmol) and AIBN (1.5 mg, 0.01 mmol) in toluene (2 mL) was purged with argon. The reaction flask was placed in a preheated oil bath at 60° C. and then heated from 60 to 90° C. over 15 min. After concentration under reduced pressure, the crude residue was purified by flash chromatography on silica gel using EtOAc/n-hexane as eluant to afford the title compound (9 mg, 70%) as a colorless oil; $R_f$=0.80 (EtOAc/n-hexane 7/3); $^1$H NMR (CDCl$_3$) δ0.75 (t, 3H, J=7.2 Hz), 0.7–0.95 (m, 2H), 1.04–1.30 (m, 3H), 1.36–1.56 (m, 2H), 1.66–1.76 (m, 1 H), 2.18 (dd, H$_{6endo}$, J$_{6en-7}$=9.6 Hz, J$_{6en-6ex}$=13.2 Hz), 2.12–2.24 (m, 1H), 2.48–2.59 (m, 1H), 2.53 (s, 3H), 2.82 (dt, 1H, J=5.1 Hz, J=13.2 Hz), 2.99 (dd, H$_7$, J$_{7-6en}$ =5.7 Hz, J$_{7-6ex}$=9.6 Hz), 3.44–3.54 (m, H$_5$), 3.66 (s, H$_1$), 7.05–7.35 (m, 5H).

The intermediate compound 14a was prepared as follows.

a. 4β-Butyl-8-methyl-2α-(phenoxythiocarbonyloxy)-3α-phenyl-8-azabicyclo[3.2.1]octane-6β-carbonitrile (14a)

To a solution of alcohol 8a (54 mg, 0.18 mmol) in THF (5 mL) at −78° C. was added n-BuLi (0.072 mL, 0.18 mmol, 2.5 M in hexane), followed immediately by phenyl thionochloroformate (0.038 mL, 0.27 mmol). After 1 h, the reaction was quenched with a saturated solution of NaHCO$_3$ (20 mL) and extracted with ether (2×20 mL). The collected organic phase was dried, concentrated under reduced pressure and the crude mixture purified by flash chromatography on silica gel using EtOAc/n-hexane as eluant to afford compound 14a (30 mg, 40%) as a colorless oil: $R_f$=0.8 (EtOAc/n-hexane 2/8); $^1$H NMR (CDCl$_3$) δ0.83 (t, 3H, J=6.6 Hz), 1.2–1.5 (m, 6H), 1.62–1.8 (m, H$_4$), 2.25–2.50 (m, H$_{7endo}$ and H$_{7exo}$), 2.57 (s, 3H), 2.77 (t, H$_6$, J=8.1 Hz), 3.07 (dd, H$_3$, J=4.8 and 10.8 Hz), 3.50 (bs, H$_5$), 3.98 (bt, H$_1$, J=δ6.6 Hz), 5.75 (dd, H$_2$, J=5.1 and 8.7 Hz), 6.84 (d, 2H, J=7.8 Hz), 7.1–7.4 (m, 8H); $^{13}$C NMR (CDCl$_3$) δ13.95, 22.62, 28.34, 28.64, 33.79, 34.12, 41.95, 44.55, 46.07, 64.15, 71.60, 76.58, 71.00, 77.42, 83.32, 121.67, 123.51, 126.62, 126.91, 128.29, 129.46, 129.76, 138.00, 153.05, 194.33.

Example 4

2β-Butyl-8-methyl-3-phenyl-8-azabicyclo[3.2.1]octane-6-exo-carbonitrile (9a and 13a)

A mixture of 10a (80 mg, 0.30 mmol) and a catalytic amount of 10% Pd/C in MeOH (7 mL) was hydrogenated under 30 psi of H$_2$ at 25° C. for 24 h. Filtration through a pad of celite and concentration under reduced pressure afforded a mixture containing the two isomers which was purified by preparative thin layer chromatography on silica gel using EtOAc/n-hexane as eluant to afford the title compounds: 13a (30 mg, 37%): colorless oil; $R_f$=0.85 (EtOAc/n-hexane 7/3); $^1$H NMR (CDCl$_3$) δ0.82 (t, 3H, J=6.6 Hz), 0.9–1.4 (m, 8H), 2.03 (dd, H$_{6endo}$, J$_{6en-7}$=9.3 Hz, J$_{6en-6ex}$=12.9 Hz), 2.3–2.6 (m, 3H), 2.49 (s,3H), 2.75 (t, H$_7$, J=8.1 Hz), 3.41 (s, H$_1$), 3.47 (bt, H$_5$, J=7.8 Hz), 7.1–7.3 (m, 5H); $^{13}$C NMR (CDCl$_3$) δ13.93, 22.71, 28.94, 33.00, 34.02, 36.23, 39.08, 40.09, 42.05, 51.47, 60.82, 71.52, 123.99, 126.21, 127.89, 128.35, 144.45; MS,m/z (%): 282 (M$^+$, 12), 239 (13), 225 (64), 172 (12), 107 (32), 42 (100); and 9a (50 mg, 63%): colorless oil; $R_f$=0.80 (EtOAc/n-hexane 7/3); $^1$H NMR (CDCl$_3$) δ0.75 (t, 3H, J=7.2 Hz), 0.7–0.95 (m, 2H), 1.04–1.30 (m, 3H), 1.36–1.56 (m, 2H), 1.66–1.76 (m, 1H), 2.18 (dd, H$_{6endo}$, J$_{6en-7}$=9.6 Hz, J$_{6en-6ex}$=13.2 Hz), 2.12–2.24 (m, 1H), 2.48–2.59 (m, 1H), 2.53 (s, 3H), 2.82 (dt, 1H, J=5.1 Hz, J=13.2 Hz), 2.99 (dd, H$_7$, J$_{7-6en}$=5.7 Hz, J$_{7-6ex}$=9.6 Hz), 3.44–3.54 (m, H$_5$), 3.66 (s, H$_1$), 7.05–7.35 (m, 5H); $^{13}$C NMR (CDCl$_3$) δ13.98, 22.60, 26.42, 29.60, 30.58, 32.21, 32.55, 36.53, 42.68, 45.91, 63.02, 71.28, 124.25, 126.21, 127.58, 127.91, 128.26, 141.95; MS, m/z (%): 282 (M$^+$, 12), 239 (13), 225 (11), 172 (20), 107 (57), 42 (100).

The intermediate compound 10a was prepared as follows.

a. 2-Hydroxy-8-methyl-3-phenyl-8-azabicyclo[3.2.1] octane-3-ene-6-exo-carbonitrile (11a)

Enone 4a (200 mg, 0.84 mmol) was dissolved in a solution of CeCl$_3$.7H$_2$O (340 mg, 0.92 mmol) in MeOH (2.3 mL), then NaBH$_4$ (32 mg, 0.84 mmol) was added portionwise. This mixture was stirred at 25° C. for 5 min then diluted with water (30 mL) and extracted with EtOAc (2×30 mL). The collected organic phases were dried and concentrated under reduced pressure. The crude material was purified by flash chromatography on silica gel using EtOAc/ n-hexane as eluant to obtain a mixture of the two alcohols (200 mg, 98%) as a white foam: $R_f$=0.8 (EtOAc/n-hexane 8/2). 2α isomer: $^1$H NMR (CDCl$_3$) δ1.83 (bs, OH), 2.32 (qd, H$_{7ex}$, J=3.3, 7.2 and 14.1 Hz), 2.66 (s, 3H), 2.77 (dd, H$_{7en}$, J=9.6 and 13.8 Hz), 3.02 (dd, H$_6$, J=3.3 and 9.6 Hz), 3.68 (t, H$_1$, J=6.0 Hz), 3.78 (d, H$_5$, J=5.4 Hz), 5.15 (d, H$_2$, J=5.1 Hz), 6.11 (d, H$_4$, J=5.4 Hz), 7.24–7.40 (m, 5H); MS, m/z (%): 240 (M$^+$, 4), 186 (2), 170 (28), 154 (3), 128 (30, 85 (4), 57 (100). 2β isomer: $^1$H NMR (CDCl$_3$) δ1.70 (bs, OH), 1.95 (dd, H$_{7en}$, J=9.9 and 14.1 Hz), 2.55 (qd, H$_{7ex}$, J=3.9, 8.1 and 14.1 Hz), 2.90 (dd, H$_6$, J=3.6 and 9.9 Hz), 3.68 (d, H$_1$, J=8.1 Hz), 3.91 (d, H$_5$, J=6.0 Hz), 4.13 (s, H$_2$), 6.33 (d, H$_4$, J=6.0 Hz), 7.24–7.45 (m, 5H); MS, m/z (%): 240 (M$^+$, 2), 186 (4), 170 (30), 115 (2), 85 (3), 57 (100).

b. 2-Acetoxy-8-methyl-3-phenyl-8-azabicyclo[3.2.1]oct-3-ene-6-exo-carbonitrile (12a)

To a solution of 11a (200 mg, 0.83 mmol) in pyridine (2 mL) was added acetic anhydride (0.31 mL, 3.33 mmol). The resulting solution was stirred at 25° C. for 15 h then concentrated under reduced pressure, diluted with EtOAc (30 mL) and washed with NH$_4$Cl (2×20 mL), dried and concentrated under reduced pressure to afford a crude mixture of the two isomers that were separated by flash chromatography on silica gel using EtOAc/n-hexane as eluant. 2α-Acetoxy isomer (180 mg, 76%): white solid; mp 107–109° C.; $R_f$=0.6 (EtOAc/n-hexane 1/1); $^1$H NMR (CDCl$_3$) δ1.91 (s, 3H), 2.34 (qd, H$_{7ex}$, J=3.0, 6.9 and 13.8 Hz), 2.64 (dd, H$_{7en}$, J=9.6 and 13.8 Hz), 2.70 (s, 3H), 3.08 (dd, H$_6$, J=3.3, 9.6 Hz), 3.76 (t, H$_1$, J=6.0 Hz), 3.81 (d, H$_5$, J=5.4 Hz), 6.25 (d, H$_4$, J=5.4 Hz), 6.30 (d, H$_2$, J=5.1 Hz), 7.15–7.22 (m, 2H), 7.27–7.36 (m, 3H), $^{13}$C NMR (CDCl$_3$) δ20.86, 28.92, 33.61, 37.23, 60.73, 63.60, 69.37, 122.37, 125.62, 128.03, 128.32, 128.43, 136.41, 136.62, 170.49; MS, m/z (%): 282 (M$^+$, 5), 223 (10), 182 (7), 170 (100), 128 (9), 115 (9); and 2β-Acetoxy isomer (50 mg, 21%): white solid; mp 134–137° C.; $R_f$=0.55 (EtOAc/n-hexane 1/1); $^1$H NMR (CDCl$_3$) δ1.97 (s, 3H), 2.03 (dd, H$_{7en}$, J=9.3 and 13.8 Hz), 2.56 (qd, H$_{7ex}$, J=3.3, 7.5 and 13.8 Hz), 2.61 (s, 3H), 2.88 (dd, H$_6$, J=3.3 and 9.3 Hz), 3.65 (d, H$_1$, J=7.5 Hz), 4.0 (d, H$_5$, J=5.4Hz), 5.42 (s, H$_2$), 6.40 (d, H$_4$, J=5.7 Hz), 7.24–7.57 (m, 5H); $^{13}$C NMR (CDCl$_3$) δ20.93, 31.13, 32.30, 38.37, 62.84, 64.03, 68.86, 122.25, 125.56, 128.36, 128.62, 128.84, 134.23, 136.32, 170.53; MS, m/z (%): 282 (M$^+$, 3), 223 (4), 186 (3), 170 (100), 154 (5), 128 (40), 127 (3), 115 (3), 57 (76).

c. 2β-Butyl-8-methyl-3-phenyl-8-azabicyclo[3.2.1]oct-3-ene-6-exo-carbonitrile (10a)

To a suspension of CuCN (4.0 mg, 0.045 mmol) in dry ether (2 mL) at −7° C. was added n-BuMgBr (0.45 mL, 0.45 mmol, 1.0 M in ether). After 10 minutes, a solution of compound 12a (60 mg, 0.22 mmol) in dry ether (3 mL) was added dropwise and the resulting mixture stirred at 25° C. for 1.5 h, diluted with ether (20 mL) and the organic phase washed with a saturated solution of NH$_4$Cl (2×20 mL), dried and concentrated under reduced pressure. The crude mixture was purified by flash chromatography on silica gel using EtOAc/n-hexane as eluant to afford compound 10a (48 mg, 80%) as a colorless oil: $R_f$=0.7 (EtOAc/n-hexane 3/7); $^1$H NMR (benzene-d$_6$) δ0.76 (t, 3H, J=6.6 Hz), 1.0–1.4 (m, 5H), 1.6–1.1.7 (m, H$_2$), 1.71 (dd, H$_{6en}$, J=9.0 and 12.0 Hz), 2.0–2.12 (m, H$_{6ex}$), 2.21 (s, 3H), 2.118–2.3 (m, H$_7$), 2.90 (t, H$_5$, J=5.4 Hz), 3.51 (s, H$_1$), 5.58 (d, H$_4$, J=5.4 Hz), 7.04–7.20 (m, 5H); $^{13}$C NMR (CDCl$_3$) δ13.94, 22.61, 30.17, 30.70, 31.85, 37.22, 41.94, 47.52, 62.16, 70.10, 123.62, 125.83, 127.52, 128.32, 128.47, 138.17, 139.39; MS, m/z (%): 280 (M$^+$, 3), 237 (2), 170 (9), 119 (100), 107 (17), 91 (14).

Example 5

2β-Butyl-7α-fluoro-8-methyl-3β-phenyl-8-azabicyclo [3.2.1]octane (59)

To a mixture of 58 (30 mg, 0.072 mmol) and Na$_2$HPO$_4$ in HPLC grade methanol was added Na-Hg (82 mg) and stirred at room temperature for 3 hours. The resultant mercury was filtered, and the filtrate was concentrated. The residue was dissolved in dichloro methane and washed with water, brine, dried and concentrated. Purification using PTLC afforded the title compound 59 (14.0 mg, 70%); $^1$H-NMR (10): (CDCl$_3$, 300 Mhz): δ0.78 (t, 3H, J=7.0), δ1.03–1.40 (m, 8H), δ1.65 (ddd, 1H, J=26.1, 14.4, 2.4), δ2.16 (s, 3H), δ2.36 (s, 3H), δ2.30–2.80 (m, 3H), δ3.13 (d, 1H, J=6.3), δ19 (t, 1H, J=8.1), δ5.30–5.60 (dddd, 1H, J=57.6, 9.3, 6.3, 2.7), δ7.25 (brm, 5H).

The intermediate compound 58 was prepared as follows.

a. 8-Methyl-2-oxo-3-phenyl-8-azabicyclo[3.2.1]oct-3-ene-6α-fluoro-6β-phenylsulfone (53)

A mixture of phenyl (1-fluorovinyl)sulfone (0.73 g, 3.986 mmol) and compound 3 (0.82 g, 4.385 mmol) in dry acetonitrile was refluxed for 20 hours under nitrogen atmosphere. The solvent was removed under reduced pressure and the residue was purified by column chromatography to give compound 53: 0.75 g (69%), compound 54: 0.054 g (5%), and compound 55: 0.087 g (8%); $^1$H-NMR (53): (CDCl$_3$, 300 Mhz): δ1.92 (dd, 1H, J=24.0, 15.3), δ2.60 (s, 3H), δ3.28 (ddd, 1H, J=22.6, 15.0, 7.5), δ3.80 (d, 1H, J=7.5), δ4.60 (d, 1H, J=5.4), δ6.80 (dd, 1H, J=1.5, 5.4), δ7.34 (s, 5H), δ7.60–8.06 (m, 5H).

b. 2-Acetoxy-8-methyl-3-phenyl-8-azabicyclo[3.2.1]oct-3-ene-6α-fluoro-6β-phenylsulfone (mixture 56)

To a solution of 53 (0.60 g, 1.6 mmol) in MeOH/DCM (20 ml, 1:1 v/v) was added CeCl$_3$.7H$_2$O (0.60 g, 1.6 mmol) and the mixture was stirred at room temperature for 30 minutes. Then NaBH$_4$ (0.06 g, 1.65 mmol) was added in portions and continued stirring for further 30 minutes. Methanol was removed under reduced pressure and the residue partitioned between aq. NH$_4$Cl and dichloro methane. The organic layer washed with water, brine, dried (Na$_2$SO$_4$) and concentrated under reduced pressure. Without any further purification, the compound was carried for next reaction. The crude alcohol (0.60 g, 1.6 mmol) was stirred with 10 ml of pyridine/aceticanhydride (2:1 v/v) for 15 hours at room temperature. The excess pyridine and acetic anhydride were removed under reduced pressure. The residue was diluted with ethyl acetate and washed with sat. NaHCO$_3$, water and dried (Na$_2$SO$_4$). The solvent was removed under reduced pressure and the residue was purified by column chromatography to afford a mixture of diasteriomers 56 in 90% yield (0.60 g). The mixture was used in sub-part c, without further purification.

c. 2β-Butyl-8-methyl-3-phenyl-8-azabicyclo[3.2.1]oct-3-ene-7α-fluoro-7β-phenylsulfone (57)

Dry CuCN (42 mg) was suspended in dry diethyl ether under inert atmosphere and cooled to –15° C. (the temperature was measured externally). n-BuMgBr (2.0 ml of 2 M solution in diethyl ether) was added dropwise and the solution was stirred for 30 minutes. A solution of 56 (420 mg, 1.01 mmol) was added through canula by maintaining the temperature at –15° C. Once the addition was complete, the mixture was warmed to room temperature and stirred for 1 hour (the reaction mixture turned dark brown). The reaction mixture was diluted with diethyl ether and washed with NH$_4$Cl/NH$_4$OH mixture (1:1), NaCl solution and dried (Na$_2$SO$_4$). The solvent was removed under reduced pressure and the residue was purified by column chromatography to give 0.34 g (80%) of compound 57 as a colorless syrup; GCMS: 413 (M$^+$), 272 (base peak); $^1$H-NMR: (CDCl$_3$, 300 Mhz): δ0.82 (t, 3H, J=7.2), δ1.10–1.40 (m, 6H), δ1.55–1.57 (brm, 1H), δ2.00 (dd, 1H, J=21.3, 14.1), δ2.70 (s, 3H), δ2.92 (ddd, 1H, J=26.2, 14.4, 5.7), δ3.54 (t, 1H, J=5.7), δ3.95 (brs, 1H), δ5.96 (d, 1H, J=5.7), δ7.26 (brm, 5H), δ7.56–8.06 (m, 5H).

d. 2β-Butyl-8-methyl-3β-phenyl-8-azabicyclo[3.2.1]octane-7α-fluoro-7β-phenylsulfone (58)

To a solution of 57 (0.30 g, 0.726 mmol) in ethyl acetate (20 ml) PtO$_2$ (10 mg) was added and stirred for 3 hours under H$_2$ pressure. The catalyst was filtered off and the filtrate was concentrated to give crude 58 as yellow color solid. Recrystallization gave 58 (270 mg, 90%) as colorless crystals; M.P. 173° C.; GCMS: 415 (M$^+$), 100 (base peak); $^1$H NMR: (CDCl$_3$, 300 Mhz): δ0.70 (t, 3H, J=7.0), δ0.85–1.41 (m, 7H), δ1.78 (dd, 1H, J=21.0, 14.1), δ2.00 (m, 1H), δ2.30 (m, 1H), δ2.58 (m, 1H), δ2.56 (s, 3H), δ2.90 (ddd, 1H, J=30.6, 14.1, 5.1), δ3.43 (brm, 1H), δ3.52 (d, 1H, J=6.0), δ7.10–8.06 (m, 10H).

Example 6

2β-Butyl-7β-fluoro-8-methyl-3β-phenyl-8-azabicyclo[3.2.1]octane (60)

The title compound was isolated from the chromatography of Example 5 gave the title compound 60 (2.0 mg, 10%); $^1$H-NMR: (CDCl$_3$, 300 Mhz): δ0.83 (t, 3H, J=7.2), δ1.03–1.40 (m, 9H), δ1.62 (brs, 2H), δ2.06 (ddd, 1H, J=21.6, 18.0, 6.6), δ2.38–2.80 (m, 3H), δ2.58 (s, 3H), δ3.20 (d, 1H, J=16.5), δ3.48 (t, 1H, J=8.1), δ5.05–5.26 (dd, 1H, J=56.1, 6.6), δ7.20 (brm, 5H).

Example 7

Synthesis of 8-methyl-2-oxo-3-phenyl-8-azabicyclo[3.2.1]oct-3-ene-6-phenylsulfone and 8-methyl-2-oxo-3-phenyl-8-azabicyclo[3.2.1]oct-3-ene-7-phenylsulfone (5a–c)

To a solution of 3 (0.59 g, 3.17 mmol) in acetonitrile (20 mL) was added phenyl vinylsulfone (1.07 g, 6.34 mmol). The resulting solution was refluxed under nitrogen for 1 h then concentrated under reduced pressure. The three isomers 5a–c present in the crude mixture were separated by flash chromatography on silica gel using EtOAc/n-hexane as eluant. 5a (60%): pale yellow solid; R$_f$=0.8 (EtOAc/n-hexane 1/1); $^1$H NMR (CDCl$_3$) δ2.01 (dd, H$_{7endo}$, J$_{7en-7ex}$=14.1 Hz, J$_{7en-6}$=9.0 Hz), 2.485 (s, 3H), 2.818 (qd, H$_{7exo}$, J$_{7ex-6}$=4.5 Hz, J$_{7ex-1}$=7.5 Hz, J$_{7ex-7en}$=12.3 Hz), 3.668 (dd, H$_6$, J$_{6-7ex}$=4.5 Hz, J$_{6-7en}$=9.0 Hz), 3.714 (d, H$_1$, J$_{1-7ex}$=7.5 Hz), 4.412 (d, H$_5$, J$_{5-4}$=5.4 Hz), 6.985 (d, H$_4$, J$_{4-5}$=5.4 Hz), 7.34 (bs, 5H), 7.55–7.63 (m, 2H), 7.64–7.72 (m, 1H), 7.91–7.98 (m, 2H); $^{13}$C NMR (CDCl$_3$) δ27.76, 34.74, 61.00, 67.70, 70.29, 128.16, 128.29, 128.62, 128.66, 129.28, 133.28, 133.95, 138.29, 138.92, 141.08, 196.85. 5b (16%): pale yellow foam; R$_f$=0.4 (EtOAc/n-hexane 8/2), $^1$H NMR (CDCl$_3$) δ2.15 (dd, H$_{7endo}$, J$_{7en-7ex}$=14.1 Hz, J$_{7en-6}$=6.9 Hz), 2.435 (s, 3H), 2.56 (qd, H$_{7exo}$, J$_{7ex-6}$=9.6 Hz, J$_{7ex-7en}$=13.8 Hz, J$_{7ex-1}$=8.1 Hz), 3.73 (d, H$_1$, J$_{1-7ex}$=7.8 Hz), 4.15 (m, H$_6$), 4.217 (t, H$_5$, J$_{5-4}$=J$_{5-6}$=5.1 Hz), 7.20 (d, H$_4$, J$_{4-5}$=5.1 Hz), 7.32–7.43 (m, 3H), 7.47–7.53(m, 2H), 7.54–7.62 (m, 2H), 7.64–7.72 (m, 1H), 7.87–7.94 (m, 2H); $^{13}$C NMR (CDCl$_3$) δ27.16, 36.65, 62.07, 67.13, 71.10, 127.90, 128.13, 128.25, 128.62, 129.5, 134.01, 139.23, 139.77, 141.60, 196.38. 5c (16%): pale yellow foam; R$_f$=0.2 (EtOAc/n-hexane 1/1); $^1$H NMR (CDCl$_3$) δ2.2 (dd, H$_{6endo}$, J$_{6en-6ex}$=13.2 Hz, J$_{6en-7}$=9.0 Hz), 2.563 (s, 3H), 2.795 (dt, H$_{6exo}$, J$_{6ex-5}$=J$_{6ex-7}$=6.6 Hz, J$_{6ex-6en}$=12.9 Hz), 3.534 (t, H$_7$, J$_{7-6ex}$=J$_{7-6en}$=8.1 Hz), 3.9–4.2 (m, H$_5$ and H$_1$), 7.034 (d, H$_4$, J$_{4-5}$=5.4 Hz), 7.324 (bs, 5H), 7.55–7.63 (m, 2H), 7.64–7.72 (m, 1H), 7.92–7.99 (m, 2H); $^{13}$C NMR (CDCl$_3$) δ30.88, 36.60, 61.35, 64.40, 71.89, 128.15, 128.23, 128.33, 128.46, 129.46, 133.37, 134.05, 137.05, 138.63, 145.29, 193.61.

Example 8

(1R,5S)-2β-n-Propyl-3β-phenyltropane (21)

A solution of n-BuLi (1.20 mL, 2.62 mmol, 1.2 M in hexane) was dissolved in THF (10 mL) and cooled to 0° C. Ethyltriphenylphosphonium bromide (0.97 g, 2.62 mmol) was added slowly under nitrogen. The resulting yellow-orange solution was stirred at 0° C. for 30 min., and then the cooling bath was removed. The crude aldehyde 18 (0.20 g, 0.87 mmol) was added in THF (2 mL), and the reaction mixture was stirred for 15 h at RT, diluted with EtOAc (20 mL) and washed with NH$_4$Cl (2×30 mL). The organic phase was extracted with HCl 10% (3×10 mL). The collected aqueous phase was washed with EtOAc (30 mL), neutralized with a saturated solution of NaHCO$_3$ and extracted with CH$_2$Cl$_2$ (2×30 mL). The collected organic phase was dried, concentrated under reduced, and the residue was purified by flash chromatography (silica gel, ether/TEA, 9.5/0.5) to afford 0.15 g (71%) of the intermediate olefin as a mixture of the cis and trans isomers.

To a solution of the intermediate olefins (0.15 g) in MeOH (10 mL) was added a catalytical amount of Pt/C 5%. The mixture was stirred at RT for 30 min. under a hydrogen atmosphere at 40 psi. The resulting solution was filtered over Celite and evaporated to dryness. The resulting colorless oil was purified by flash chromatography (silica gel, ether/TEA, 9.5/0.5) to afford the 0.13 g (95%) of 21 as a colorless oil: [α]$^{25}_D$ –97° (c=0.5, CH$_2$Cl$_2$); $^1$H NMR (CDCl$_3$) δ 0.71 (t, 3H, J=7.2 Hz), 0.78–0.95 (m, 1H), 1.20–1.35 (m, 1H), 1.38–1.56 (m, 2H), 1.56–1.75 (m, 3H), 1.97–2.26 (m, 3H), 2.25 (s, 3H), 3.07 (dt, 1H, J=5.1 and 13.2 Hz), 3.12–3.20 (m, 1H), 3.20–3.29 (m, 1H), 7.10–7.35 (m, 5H); $^{13}$C NMR (CDCl$_3$) δ 14.2, 20.8, 24.8, 26.4, 29.3, 33.6, 36.4, 42.1, 46.0, 62.0, 64.7, 125.6, 127.8, 128.0, 143.8: MS m/z (%) 243 (M$^+$, 11), 214 (8), 82 (100).

The intermediate aldehyde 18 was prepared as follows.

a. Methyl (1R,5S)-3β-phenyltropane-2β-carboxylate (15)

Compound 15 was prepared from (−)-cocaine by a procedure analogous to that reported by Kozikowski and co-worker (*J. Med. Chem.* 1995, 38, 3086–3093); a colorless oil: $^1$H NMR (CDCl$_3$) δ1.54–1.78 (m, 3H), 2.02–2.24 (m, 2H), 2.23 (s, 3H), 2.60 (dt, 1H, J=2.7 and 12.6 Hz), 2.92 (t, 1H, J=3.6 Hz), 3.00 (dt, 1H, J=5.1 and 12.6 Hz), 3.33–3.42 (m, 1H), 3.48 (s, 3H), 3.52–3.60 (m, 1H), 7.10–7.30 (m, 5H); $^{13}$C NMR (CDCl$_3$) δ25.2, 25.9, 33.7, 33.9, 42.0, 51.1, 52.8, 62.3, 65.3, 125.8, 127.3, 127.9, 143.0, 172.1. Anal. (C$_{16}$H$_{21}$NO$_2$) C, H, N.

b. (1R,5S)-2β-formyl-3β-phenyltropane (18)

To a solution of 15 (0.50 g, 1.93 mmol) in THF (20 mL) was added portionwise LiAlH$_4$ (0.15 g, 3.85 mmol). The resulting mixture was stirred at RT for 2 h then a saturated solution of Rochelle salt (30 mL) was added followed by extraction with EtOAc (100 mL). The organic phase was washed with brine (100 mL), dried and concentrated under reduced pressure to afford 0.35 g (79%) of the alcohol intermediate as a white solid: $^1$H NMR (CDCl$_3$) δ1.43–50 (m, 1H), 1.57–1.66 (m, 1H), 1.73 (d, 1H, J=8.1 Hz), 1.67–1.80 (m, 1H), 2.04–2.24 (m, 2H), 2.27 (s, 3H), 2.51 (dt, 1H, J=2.7 and 12.9 Hz), 3.05 (dt, 1H, J=6.0 and 13.2 Hz), 3.28–3.35 (m, 1H), 3.39 (dd, 1H, J=2.1 and 10.8 Hz), 3.42–3.50 (m, 1H), 3.74 (dd, J=2.1 and 11.1 Hz), 7.10–7.40 (m, 5H); MS m/z 231 (M$^+$, 12), 200 (14), 172 (12), 82 (100).

Oxalyl chloride (0.10 mL, 1.08 mmol) was dissolved in anhydrous CH$_2$Cl$_2$ (10 mL), and the solution was cooled to −78° C. Dimethyl sulfoxide (0.15 mL, 2.16 mL) was added, after 5 min. the above alcohol (0.25 g, 1.08 mmol) was added in CH$_2$Cl$_2$ (5 mL), and stirring was continued for 30 min. The reaction mixture was quenched by adding Et$_3$N (1.4 mL), and the resulting solution was warmed to RT, diluted with CH$_2$Cl$_2$ (30 mL) and washed with NH$_4$Cl (2×30 mL), dried and concentrated under reduced pressure to provide 0.21 g (84%) of 18 as a colorless oil used in the next step without further purification: $^1$H NMR (CDCl$_3$) δ1.70 (d, 1H. J=8.4 Hz), 1.63–1.78 (m, 1H), 1.91 (dt, 1H, J=3.6 and 12.9), 2.19 (s, 3H), 2.10–2.28 (m, 2H), 2.40–2.56 (m, 2H), 3.18 (dt, 1H, J=5.4 and 13.2 Hz), 3.38–3.45 (m, 1H), 3.48–3.55 (m, 1H), 7.15–7.40 (m, 5H), 9.65 (d, 1H, J=3.0 Hz).

Example 9
(1R,5S)-2β-n-Propyl-3β-(p-tolyl)tropane (22)

Using a procedure similar to that described in Example 8, except replacing the compound 18 used therein with compound 19, the title compound 22 was prepared as a colorless oil: [α]$^{25}_D$ −82° (c 0.5, CH$_2$Cl$_2$); $^1$H NMR (CDCl$_3$) δ0.72 (t, 3H, J=7.2 Hz), 0.80–0.96 (m, 1H), 1.20–1.36 (m, 1H), 1.39–1.56 (m, 2H), 1.56–1.75 (m, 3H), 1.96–2.26 (m, 3H), 2.25 (s, 3H), 2.31 (s, 3H), 3.04 (dt, 1H, J=4.8 and 13.2Hz), 3.12–3.20 (m, 1H), 3.20–3.29 (m, 1H), 7.02 (d, 2H, J=8.1 Hz), 7.08 (d, 2H, J=8.1 Hz); $^{13}$C NMR (CDCl$_3$) δ14.1, 20.7, 20.9, 24.8, 26.4, 29.1, 33.7, 35.9, 42.0, 45.9, 62.1, 64.7, 127.6, 128.7, 135.0, 140.5.

The intermediate compound 19 was prepared as follows.
a. Methyl (1R,5S)-3β-(p-tolyl)tropane-2β-carboxylate (16)

Compound 15 was prepared from (−)-cocaine by a procedure analogous to that reported by Kozikowski and co-worker (*J. Med. Chemn.* 1995, 38, 3086–3093); a colorless oil:$^1$H NMR (CDCl$_3$) δ1.54–1.78 (m, 3H), 2.00–2.24 (m, 2H), 2.22 (s, 3H), 2.29 (s, 3H), 2.58 (dt, 1H, J=2.7 and 12.3 Hz), 2.89 (t, 1H, J=3.6 Hz), 2.97 (dt, 1H, J=4.8 and 12.9 Hz), 3.32–3.40 (m, 1H), 3.49 (s, 3H), 3.52–3.60 (m, 1H), 7.07 (d, 2H, J=7.8 Hz), 7.14 (d, 2H, J=7.8 Hz); $^{13}$C NMR (CDCl$_3$) δ21.0, 25.2, 25.9, 33.9, 33.3, 34.1, 42.0, 51.1, 52.8, 62.3, 65.3, 127.1, 128.6, 135.1, 139.9, 172.2.

b. (1R,5S)-2β-formyl-3β-(p-tolyl)tropane (19)

Using a procedure similar to that described in Example 8, sub-part b, except replacing the compound 15 used therein with compound 16, the title compound 19 was prepared as a colorless oil: $^1$H NMR (CDCl$_3$) δ1.70 (d, 1H. J=8.7 Hz), 1.60–1.78 (m, 1H), 1.89 (dt, 1H, J=3.9 and 12.9), 2.19 (s, 3H), 2.30 (s, 3H), 2.10–2.33 (m, 2H), 2.39–2.53 (m, 2H), 3.14 (dt, 1H, J=5.7 and 12.9 Hz), 3.36–3.45 (m, 1H), 3.46–3.55 (m, 1H), 7.10 (br s, 4H), 9.66 (d, 1H, J=3.3 Hz).

Example 10
(1R,5S)-2β-n-Butyl-3β-(p-tolyl)tropane (23)

Using a procedure similar to that described in Example 8, except replacing the compound 18 used therein with compound 19, and replacing the ethyl phosphonium salt with the corresponding propyl phosphonium salt, the title compound 23 was prepared as a colorless oil: [α]$^{25}_D$ −76° (c 1.5, CH$_2$Cl$_2$); $^1$H NMR (CDCl$_3$) δ0.74 (t, 3H, J=7.2 Hz), 0.70–0.90 (m, 2H), 1.12–1.30 (m, 3H), 1.39–1.68 (m, 5H), 1.96–2.20 (m, 3H), 2.24 (s, 3H), 2.31 (s, 3H), 3.03 (dt, 1H, J=5.1 and 13.2 Hz), 3.12–3.20 (m, 1H), 3.20–3.28 (m, 1H), 7.03 (d, 2H, J=8.1 Hz), 7.08 (d, 2H, J=8.1 Hz); $^{13}$C NMR (CDCl$_3$) δ14.2, 21.0, 22.7, 24.8, 26.4, 26.7, 30.1, 33.8, 36.0, 42.1, 46.2, 62.1, 64.7, 127.7, 128.7, 135.0, 140.7; MS m/z (%) 271 (M$^+$, 6), 242 (2), 214 (4), 96(40), 83 (100).

Example 11
(1R,5S)-2β-n-Propyl-3β-(p-flurophenyl)tropane (24)

Using a procedure similar to that described in Example 8, except replacing the compound 18 used therein with compound 20, the title compound 24 was prepared as a colorless oil: [α]$^{25}_D$ −60.4° (c 2, CHCl$_3$); $^1$H NMR (CDCl$_3$) δ0.60–0.78 (m, 1H), 0.74 (t, 3H, J=7.2 Hz), 0.80–0.96 (m, 1H), 1.20–1.36 (m, 1H), 1.39–1.76 (m, 5H), 1.95–2.25 (m, 3H), 2.26 (s, 3H), 3.07 (dt, 1H, J=4.8 and 13.2 Hz), 3.14–3.22 (m, 1H), 3.22–3.30 (m, 1H), 6.98 (t, 2H, J=8.7 Hz), 7.10 (dd, 2H, J=6.0 and 8.4 Hz); $^{13}$C NMR (CDCl$_3$) δ14.1, 20.7, 24.7, 26.3, 29.1, 33.7, 35.6, 42.0, 46.0, 62.0, 64.7, 114.7 (d, J$_{C-F}$=83,1 Hz), 128.9 (d, J$_{C-F}$=30.6 Hz), 139.2 (d, J$_{C-F}$=12.9 Hz), 161.0 (d, J$_{C-F}$=970 Hz).

The intermediate compound 20 was prepared as follows.
a. Methyl (1R,5S)-3β-(p-fluorophenyl)tropane-2β-carboxylate (17)

Compound 17 was prepared from (−)-cocaine by a procedure analogous to that reported by Kozikowski and co-worker (*J. Med. Chem.* 1995, 38, 3086–3093); a colorless oil: $^1$H NMR (CDCl$_3$) δ1.56–1.80 (m, 3H), 2.00–2.24 (m, 2H), 2.23 (s, 3H), 2.56 (dt, 1H, J=2.4 and 12.6 Hz), 2.86 (t, 1H, J=3.3 Hz), 2.97 (dt, 1H, J=5.1 and 12.6 Hz), 3.32–3.40 (m, 1H), 3.50 (s, 3H), 3.52–3.60 (m, 1H), 6.95 (t, 2H, J=8.4 Hz), 7.21 (dd, 2H, J=5.7 and 8.1 Hz); $^{13}$C NMR (CDCl$_3$) δ25.1, 25.8, 33.2, 34.2, 41.9, 51.1, 52.8, 62.2, 65.2, 114.5 (d, J$_{C-F}$=83.1 Hz), 128.7 (d, J=30.6 Hz).

b. (1R,5S)-2β-formyl-3β-(p-fluorophenyl)tropane (20)

Using a procedure similar to that described in Example 8, sub-part b, except replacing the compound 15 used therein with compound 17, the compound 20 was prepared as a colorless oil: $^1$H NMR (CDCl$_3$) δ1.74 (d,1H, J=8.5), 1.64–1.82 (m,1H), 1.91 (dt,1H, J=3.8 and 12.7), 2.21 (s,3H), 2.10–2.33 (m,2H), 2.39–2.54 (m,2H), 3.16 (dt,1H, J=5.7 and 12.9), 3.40–3.48 (m,1H), 3.50–3.60 (m,1H), 7.00 (t, 2H, J=8.7), 7.19 (dd, 2H, J=6.0 and 8.4), 9.64 (d,1H, J=3.2).

Example 12
(1R, 5S)-2β-Phenyl-3α-(p-tolyl)tropane (37)

Phosphorous trichloride (61 μL, 0.70 mmol) was added to a solution of 34 (50 mg, 0.12 mmol) in dry DMF (2.00 mL) at 0° C. After being stirred at 0° C. for 1 h, the reaction was quenched with a saturated solution of NaHCO$_3$ (20 mL) and extracted with ether (2×20 mL). The collected organic phase was washed with water (30 mL), brine (30 mL), dried and concentrated under reduced pressure to afford 30 mg (61%) of the sulfide intermediate as a colorless oil used in the next step without further purification: R$_f$0.5 (EtOAc/hexane 1/9). $^1$H NMR (CDCl$_3$) δ1.34 (dt, 1H. J=1.8 and 14.1 Hz), 2.10–2.35 (m, 2H), 2.23 (s, 3H), 2.42 (ddd, 1H, J=6.9, 10.2, and 13.8 Hz), 2.62 (s, 3H), 2.65 (d, 1H, J=10.5 Hz), 2.98–3.12 (m, 1H), 3.36 (br s, 1H), 3.50–3.60 (m, 1H), 3.70 (t, 1H, J=7.8 Hz), 6.85 (d, 2H, J=7.8 Hz), 6.94 (d, 2H, J=7.8 Hz), 7.02–7.26 (m, 9H); $^{13}$C NMR (CDCl$_3$) δ20.9, 39.0, 39.5, 42.1, 43.2, 52.7, 58.8, 60.5, 75.5, 125.9, 127.2, 127.9, 128.0, 128.7, 129.2, 129.6, 134.4, 135.4, 135.7, 140.9, 146.6.

Raney-Ni was added to a solution of the sulfide (30 mg, 0.07 mmol) in ethanol (4 mL) and the resulting mixture was refluxed for 1 h. Filtration through a pad of celite and concentration under reduced pressure afforded a crude mixture that was purified by flash chromatography on silica gel using ether/Et$_3$N (9.5/0.5) as eluent to afford 15 mg (73%) of 22 as a colorless oil: [α]$^{25}_D$ –118° (c 0.3, CH$_2$Cl$_2$); $^1$H NMR (CDCl$_3$) δ1.32 (t, 1H, J=12.3 Hz), 1.50–1.75 (m, 2H), 2.10–2.38 (m, 2H), 2.23 (s, 3H), 2.31 (s, 3H), 2.44 (d, 1H, J=10.8 Hz), 2.42–2.56 (m, 1H), 2.97 (dt, 1H, J=7.2 and 11.4 Hz), 3.27 (d, 1H, J=6.6Hz), 3.36 (t, J=6.6 Hz), 6.84 (d, 2H, J=7.8 Hz), 6.93 (d, 2H, J=7.8 Hz), 7.02–7.20 (m, 5H); $^{13}$C NMR (CDCl$_3$) δ20.9, 29.7, 29.8, 41.1, 41.3, 43.0, 58.6, 59.5, 68.1, 125.6, 127.3, 127.9, 128.1, 128.6, 135.1, 141.5, 147.6; MS m/z (%) 291 (M$^+$, 1), 178 (4), 115 (6), 96 (59), 82 (100).

The intermediate compound 34 was prepared as follows.

a. 1-Methyl-4-(p-tolyl)-3-pyridiniumolate (26)

Using a procedure similar to that described by Kozikowski and co-worker, *J. Org. Chem.* 1997, 62, 503–509, compound 26 was prepared;: mp 185° C. (dec); $^1$H NMR (CDCl$_3$) δ2.38 (s, 3H), 3.94 (s, 3H), 6.95 (dd, 1H, J=2.1 and 6.0 Hz), 7.24 (d, 2H, J=8.1 Hz), 7.36 (d, 1H, J=6.0 Hz), 7.43 (d, 1H, J=1.8 Hz), 7.89 (d, 2H, J=8.4 Hz).

b. N-Methyl (1S,5S,6R, R$_S$)-3-(p-tolyl)-6-p-tolylsulphinyl)-8-azabicyclo[3.2.1]oct-3-en-2-one (29)

A solution of 1-methyl-4-(p-tolyl)-3-pyridiniumolate 26 (1.86 g, 8.37 mmol) and (+)-(R)-p-tolyl vinyl sulphoxide (1.07 g, 6.45 mmol) in dioxane (50 mL) was allowed to reflux for 20 hours. The resulting reaction mixture was concentrated under reduced pressure, purified by silica gel flash chromatography, and recrystallized from EtOAc to give the compound 29 as a white solid: [α]$^{25}_D$ –47° (c 0.8, CH$_2$Cl$_2$); R$_f$0.6 (EtOAc); mp 188° C.

c. N-Methyl (1S,5R,7R,R$_S$)-4β-phenyl-3α-(p-tolyl)-6β-(p-tolylsulphinyl)-8-azabicyclo[3.2.1]octan-2-one (31)

To a cooled (–78° C.) mixture of PhMgBr (0.55 mL, 1.64 mmol, 3.0 M in ether), HMPA (0.57 mL, 3.28 mmol), and CuBr.Me$_2$S (14.00 mg, 0.07 mmol) was added dropwise a mixture of 29 (500 mg, 1.37 mmol) and Me$_3$SiCl (0.35 mL, 2.74 mmol) in dry THF (20 mL). After 1 h, the reaction was quenched with a 20% solution of NH$_4$OH (20 mL), and the mixture was extracted with EtOAc (30 mL). The organic phase was washed with brine (30 mL), dried, and concentrated under reduced pressure. The crude mixture containing the silyl enol ether intermediate was diluted with MeOH (10 mL), and potassium fluoride was added (160 mg, 2.74 mmol). The resulting solution was stirred at RT for 5 min, then concentrated under reduced pressure. The crude mixture was purified by flash chromatography on silica gel using EtOAc/hexane as eluent to afford 130 mg (22%) of the compound 31 as a pale yellow foam: R$_f$0.65 (EtOAc/hexane 1/1); $^1$H NMR (CDCl$_3$) δ2.04 (dd, 1H, J=8.7 and 11.7 Hz), 2.24 (s, 3H), 2.20–2.34 (m, 1H), 2.41 (s, 3H), 2.56 (s, 3H), 3.10 (t, 1H, J=8.4 Hz), 3.75 (d, 1H, J=5.7 Hz), 3.85 (s, 1H), 4.09 (d, 1H, J=8.4 Hz), 6.66 (d, 2H, J=8.1 Hz), 6.99 (d, 2H, J=7.8 Hz), 7.01–7.10 (m, 2H), 7.10–7.20 (m, 3H), 7.30 (d, 2H, J=8.1 Hz), 7.55 (d, 2H, J=8.1 Hz); $^{13}$C NMR (CDCl$_3$) δ21.0, 21.4, 29.0, 39.7, 55.8, 58.2, 68.8, 72.3, 73.1, 76.6, 77.0, 77.2, 77.4, 124.1, 126.8, 127.0, 128.3, 129.0, 129.1, 130.1, 133.1, 136.5, 140.7, 142.0, 143.9, 211.7.

d. (1S,5R,7R,R$_S$)-2β-phenyl-3α-(p-tolyl)-6β-(p-tolylsulphynil)tropane (34)

To a suspension of LAH (22 mg, 0.59 mmol) in dry THF (6 mL) was added a solution of 31 (130 mg, 0.29 mmol) in dry ether (20 mL). The resulting solution was stirred at RT for 1 h, then quenched with a saturated solution of NH$_4$Cl. The resulting mixture was extracted with ether (2×50 mL). The combined organic phases were washed with brine (80 mL), dried, and concentrated under reduced pressure. The crude mixture was purified by flash chromatography on silica gel using EtOAc/hexane 6/4 as eluent to afford 120 mg (92%) of the correspondent 2α-hydroxy derivatives intermediate as a colorless oil: R$_f$0.70 (EtOAc/hexane, 8/2); $^1$H NMR (CDCl$_3$) δ1.32 (br s, 1H), 1.72–1.88 (m, 1H), 2.2 (s, 3H), 2.41 (s, 3H), 2.51 (s, 3H), 2.40–2.60 (m, 1H), 2.70 (d, 1H, J=11.4 Hz), 3.31 (8.1 Hz), 3.42 (dd, 1H, J=4.2 and 10.8 Hz), 3.56 (br s, 1H), 3.69 (t, 1H, J=6.6 Hz), 4.20–4.30 (m, 1H), 6.90–7.10 (m, 9H), 7.29 (d, 2H, J=8.1 Hz), 7.55 (d, 2H, J=8.1 Hz).

To a solution of diisopropylamine (45 μL, 0.32 mmol) in dry THF (4 mL) was added dropwise at 0° C. a solution of n-BuLi (134 μL, 0.29 mmol, 2.2 M in hexane). The resulting solution was stirred at 0° C. for 15 min. then cooled at –78° C. and a solution of the alcohol intermediate (110 mg, 0.25 mmol) in THF (5 mL) was added dropwise followed, after 5 min., by phenyl thionochloroformate (68 μL, 0.49 mmol). After 1 h, the reaction was quenched with a saturated solution of NH$_4$Cl (20 mL), and the mixture was extracted with ether (2×20 mL). The collected organic phases were dried and concentrated under reduced pressure, and the crude mixture was purified by flash chromatography on silica gel using EtOAc/hexane as eluent to afford 100 mg of the phenoxy(thiocarbonyl)oxy derivative as a colorless oil: R$_f$0.7 (EtOAc/hexane 1/1); $^1$H NMR (CDCl$_3$)δ1.90(dd, 1H, J=8.1 and 13.2 Hz), 1.95–2.09(m, 1H), 2.23 (s, 3H), 2.44 (s, 3H), 2.52 (s, 3H), 2.60 (d, 1H, J=11.1 Hz), 3.20 (t, 1H, J=7.5 Hz), 3.5 (br s, 1H), 3.64 (dd, 1H, J=5.1 and 11.1 Hz), 3.90–4.05 (m, 1H), 5.84 (dd, 1H, J=4.8 and 8.7 Hz), 6.76 (d, 2H, J=7.5 Hz), 6.82–7.42 (m, 14H), 7.56 (d, 2H, J=8.1 Hz).

A solution of the above intermediate (95 mg), Bu$_3$SnH (133 μL, 0.49 mmol), and AIBN (16 mg, 0.01 mmol) in toluene (6 mL) was purged with argon. The reaction flask was placed in a preheated oil bath at 60° C. and then heated to 90° C. for 1 h. After concentration under reduced pressure, the crude residue was purified by flash chromatography on silica gel using EtOAc/hexane as eluent to afford 53 mg (50%) of the compound 34 as a colorless oil: R$_f$0.3 (EtOAc/hexane, 3/7); $^1$H NMR (CDCl$_3$) δ0.90 (t, 1H, J=12.3 Hz), 1.18–1.40 (m, 2H), 1.52 (dd, 1H, J==8.1 and 13.2 Hz), 2.08–2.20 (m, 1H), 2.22 (s, 3H), 2.40 (s, 3H), 2.51 (s, 3H), 3.00–3.18 (m, 1H), 3.31 (t, 1H, J=7.8 Hz), 3.40–3.55 (m, 1H), 3.62 (br s, 1H), 6.80 (d, 2H, J=8.1 Hz), 6.84–6.98 (m, 4H), 7.00–7.18 (m, 3H), 7.29 (d, 2H, J=8.1 Hz), 7.56 (d, 2H, J=8.1 Hz).

Example 13

(1R,5S)-2β-Phenyl-3α-(p-fluorophenyl)tropane (38)

Using a procedure similar to that described in Example 12, except replacing the compound 34 used therein with compound 35, the title compound 38 was prepared as a colorless oil: $[\alpha]^{25}{}_D$ −104° (c 0.4, CHCl$_3$); $^1$H NMR (CDCl$_3$) δ1.30 (t, 1H, J=13.2 Hz), 1.50–1.75 (m, 2H), 2.10–2.56 (m, 4H), 2.23 (s, 3H), 2.32 (s, 3H), 2.99 (dt, 1H, J=7.5 and 11.7 Hz), 3.28 (d, 1H, J=6.6), 6.80 (t, 2H, J=8.7 Hz), 6.89 (dd, 2H, J=5.7 and 8.4 Hz), 7.00–7.20 (m, 5H).

The intermediate compound 35 was prepared as follows.

a. 1-Methyl-4-(p-fluorophenyl)-3-pyridiniumolate (27)

Using a procedure similar to that described by Kozikowski and co-worker, *J. Org. Chem.* 1997, 62, 503–509, compound 27 was prepared; mp 172° C. (dec); $^1$H NMR (CDCl$_3$) δ3.97 (s, 3H), 7.03–7.20 (m, 3H), 7.34 (d, 1H, J=6.3 Hz), 7.54 (s, 1H), 7.90–8.00 (m, 2H).

b. N-Methyl (1S,5S,6R,R$_S$)-3-(p-fluorophenyl)-6-(p-tolylsulphinyl)-8-azabicyclo[3.2.1]oct-3-en-2-one (30)

A solution of 1-methyl-4-(p-fluorophenyl)-3-pyridiniumolate 27 (2.45 g, 12.04 mmol) and (+)-(R)-p-tolyl vinyl sulphoxide (2.00 g, 12.04 mmol).in dioxane (25 mL) was allowed to reflux for 20 hours. The resulting reaction mixture was concentrated under reduced pressure, purified by silica gel flash chromatography, and recrystallized from EtOAc to give the compound 30 as a white solid; $[\alpha]^{25}{}_D$ −77° (c 1.25, CHCl$_3$); R$_f$0.2 (EtOAc/hexane, 7/3); mp 186° C. (EtOAc); $^1$H NMR (CDCl$_3$) δ1.64 (dd, H$_{7\alpha}$, J=8.7 and 14.7 Hz), 2.14 (ddd, H$_{7\beta}$, J=3.6, 7.8 and 14.7 Hz), 2.42 (s, 3H), 2.62 (s, 3H), 3.33 (dd, H$_6$, J=3.6 and 8.7 Hz), 3.73 (d, H$_1$, J=7.5 Hz), 4.51 (d, H$_5$, J=5.4 Hz), 7.01 (d, H$_4$, J=5.4 Hz), 7.041 (t, 2H, J=8.7 Hz), 7.30–7.40 (m, 4H), 7.66 (d, 2H, J=8.1 Hz).

c. N-Methyl (1S,5R,7R,R$_S$)-4β-phenyl-3α(p-fluorophenyl)-6β-(p-tolylsulphinyl)-8-azabicyclo[3.2.1]octan-2-one (32)

Using a procedure similar to that described in Example 12, sub-part c, except replacing the compound 29 used therein with compound 30, the compound 32 was prepared as colorless oil; $[\alpha]^{25}{}_D$ +203° (c 1.5, CHCl$_3$); $^1$H NMR (CDCl$_3$) δ2.03 (dd, 1H, J=8.7 and 11.7 Hz), 2.25 (dd, 1H, J=6.9 and 8.1 Hz), 2.31 (d, 1H, J=9.0 Hz), 2.40 (s, 3H), 2.57 (s, 3H), 3.09 (t, 1H, J=8.4 Hz), 3.74 (d, 1H, J=5.7 Hz), 3.85 (s, 1H), 4.14 (d, 1H, J=9.0 Hz), 6.73 (dd, 2H, J=5.4 and 8.4 Hz), 6.86 (t, 2H, J=8.7 Hz), 6.98–7.08 (m, 2H), 7.12–7.20 (m, 3H), 7.30 (d, 2H, J=8.1 Hz), 7.55 (d, J=8.1 Hz).

d. (1S,5R,7R,R$_S$)-2β-phenyl-3α-(p-fluorophenyl)-6β-(p-tolylsulphynil) tropane (35)

Using a procedure similar to that described in Example 12, sub-part d, except replacing the compound 31 used therein with compound 32, the compound 35 was prepared as colorless oil; $[\alpha]^{25}{}_D$ +107° (c 1.5, CHCl$_3$); R$_f$0.45 (EtOAc/hexane, 1/1); $^1$H NMR (CDCl$_3$) δ1.12–1.40 (m, 2H), 1.60 (dd, 1H, J==8.7 and 12.9 Hz), 2.04–2.20 (m, 1H), 2.30 (d, 1H, J=10.2 Hz), 2.24–2.45 (m, 1H), 2.39 (s, 3H), 2.50 (s, 3H), 3.06 (ddd, 1H, J=6.9, 10.5, and 12.6 Hz), 3.28 (t, 1H, J=8.4 Hz), 3.42–3.55 (m, 1H), 3.63 (br s, 1H), 6.73–6.94 (m, 6H), 7.02–7.16 (m, 3H), 7.27 (d, 2H, J=8.1 Hz), 7.55 (d, 2H, J=8.1 Hz).

Example 14

(1R,5S)-2β-n-Propyl-3α-(p-fluorophenyl)tropane (39)

Using a procedure similar to that described in Example 12, except replacing the compound 34 used therein with compound 36, the title compound 39 was prepared as colorless oil: $[\alpha]^{25}{}_D$ −40° (c 0.3, CHCl$_3$); $^1$H NMR (CDCl$_3$) δ0.77 (t, 3H, J=7.2 Hz), 1.00–1.56 (m, 8H), 2.02–2.26 (m, 2H), 2.23 (s, 3H), 2.30–2.44 (m, 1H), 2.44–2.60 (m, 1H), 2.94 (d, 1H, J=5.1), 3.21 (t, 1H, J=6.3 Hz), 6.94 (t, 2H, J=9.0 Hz), 7.06–7.20 (m, 2H).

The intermediate compound 36 was prepared as follows.

a. N-Methyl (1S,5R,7R,R$_S$)-4β-n-propyl-3α-(p-fluorophenyl)-6β-(p-tolylsulphinyl)-8-azabicyclo[3.2.1]octan-2-one (33)

Using a procedure similar to that described in Example 12, sub-part c, except replacing the compound 29 used therein with compound 30 and replacing the phenyl magnesium bromide with propyl magnesium bromide, the compound 33 was prepared as a pale yellow oil: $[\alpha]^{25}{}_D$ −71° (c 0.5, CHCl$_3$); $^1$H NMR (CDCl$_3$) δ0.66 (t, 3H, J=7.2 Hz), 0.70–0.90 (m, 1H), 1.10–1.36(m, 3H), 1.40–1.55 (m, 1H), 1.98 (dd, 1H, J=8.7 and 11.7 Hz), 2.20–2.35 (m, 1H), 2.42 (s, 3H), 2.53 (s, 3H), 2.92 (t, 1H, J=8.4 Hz), 3.54 (d, 1H, J=8.4 Hz), 3.61 (d, 1H, J=6.6 Hz), 3.64 (s, 1H), 6.89 (dd, 2H, J=5.4 and 8.4 Hz), 7.00 (t, 2H, J=8.7 Hz), 7.34 (d, 2H, J=8.1 Hz), 7.56 (d, J=8.1 Hz).

b. (1S,5R,7R,R$_s$)-2β-n-Propyl-3α-(p-fluorophenyl)-6β-(p-tolylsulphynil)tropane (36)

Using a procedure similar to that described in Example 12, sub-part d, except replacing the compound 32 used therein with compound 33, the compound 36 was prepared as colorless oil; $[\alpha]^{25}{}_D$ +82° (c 0.5, CHCl$_3$); R$_f$0.3 (EtOAc/hexane, 1/1); $^1$H NMR (CDCl$_3$) δ0.62 (t, 3H, J=6.3 Hz), 0.68–0.90 (m, 1H), 1.00–1.30 (m, 6H), 1.53 (dd, 1H, J=8.4 and 12.6 Hz), 2.00–2.15 (m, 1H), 2.20–2.60 (m, 2H), 2.38 (s, 3H), 2.44 (s, 3H), 3.17 (t, 1H, J=8.1 Hz), 3.28–3.42 (m, 1H), 3.39 (br s, 1H), 6.89 (t, 2H, J=8.7 Hz), 7.03 (dd, 2H, J=5.7 and 8.7 Hz), 7.30 (d, 2H, J=8.1 Hz), 7.56 (d, 2H, J=8.1 Hz); $^{13}$C NMR (CDCl$_3$) δ14.1, 19.4, 21.3, 32.0, 36.7, 39.4, 40.5, 41.3, 52.1, 60.5, 65.0, 72.5, 114.9 (d, J$_{C-F}$=85.2 Hz), 124.3, 129.3 (d, J$_{C-F}$=30.6 Hz), 129.9, 140.6 (d, J$_{C-F}$=11 Hz), 141.2, 141.4, 161.2 (d, J$_{C-F}$=970 Hz).

Example 15

(1R,5S)-2β-n-propyl-3β-phenyltropane (21)

Raney-Ni was added to a solution of 42 (70 mg, 0.19 mmol) in ethanol (4 mL) and the resulting mixture was refluxed for 2 h. Filtration through a pad of celite and concentration under reduced pressure afforded a mixture containing the two isomers 21 and 47 (ratio 75/25 at the GCMS analysis) which were separated by preparative thin layer chromatography on silica gel using EtOAc/hexane/Et$_3$N (8/90/2) as eluent to afford the title compound 21 (6.0 mg, 13%) as a colorless oil: $[\alpha]^{25}{}_D$ −95° (c 0.25, CH$_2$Cl$_2$).

The intermediate compound 42 was prepared as follows.

a. 1-Methyl-4-phenyl-3-hydroxypyridine (25)

A mixture of 2 (4.03 g, 12.9 mmol) and IRA-OH (400) resin (20 mL) in MeOH was stirred at 25° C. for 1 h then the basic resin was filtered off and washed several time with MeOH. The resulting clear solution was concentrated under reduced pressure to afford the compound 3 (2.21 g, 92%) as a pale yellow solid used in the next step without further purification: mp 154–157° C.; $^1$H NMR (DMSO-d$_6$) δ3.97 (s, 3H), 7.3–7.52 (m, 5H), 7.38 (d, 1H, J=7.5 Hz), 8.04 (d, 1H, J=8.1 Hz), 8.053 (s, 1H).

b. N-Methyl (1S,5S,6R,R$_s$)-3-phenyl-6-(p-tolylsulphinyl)-8-azabicyclo[3.2.1]oct-3-en-2-one (28)

To a solution of 1-methyl-4-phenyl-3-pyridiniumolate 25 (1.85 g, 10 mmol) in dioxane (50 mL) was added (+)-(R)-p-tolyl vinyl sulphoxide (1.61 g, 10 mmol). The resulting solution was refluxed for 20 h, then concentrated under reduced pressure. dioxane at reflux for 20 h to give a mixture of both exo and endo cycloadducts (70:30). Silica gel flash column chromatography of the crude mixture leads to the separation of the 6-exo products (4:1 mixture of diastereoisomers; 55% overall yield) from the 6-endo product (one diastereisomer, 22% yield). The major 6-exo diastereomer 28 was obtained by crystallisation from EtOAc of the 4:1 mixture: $[\alpha]^{25}{}_D$ −51° (c=0.5, acetone); R$_f$0.6 (EtOAc); mp 166° C. (EtOAc); $^1$H NMR (CDCl$_3$) δ1.64 (dd, H$_{7\alpha}$, J=8.7 and 14.7 Hz), 2.14 (ddd, H$_{7\beta}$, J=3.6, 7.5 and 14.7 Hz), 2.42 (s, 3H), 2.63 (s, 3H), 3.34 (dd, H$_6$, J=3.3 and 8.7 Hz), 3.74

(d, H$_1$, J=7.5 Hz), 4.51 (d, H$_5$, J=5.4 Hz), 7.02 (d, H4, J=5.1 Hz), 7.3–7.4 (m, 7H), 7.67 (d, 2H, J=8.1 Hz); $^{13}$C NMR (CDCl$_3$) δ21.5, 26.4, 34.7, 60.4, 69.3, 70.1, 125.4, 128.1, 128.3, 128.5, 130.2, 133.5, 138.6, 139.4, 141.3, 142.7, 197.0.

c. N-Methyl (1S,5S,6R)-2-acetoxy-3-phenyl-6β-(p-tolylsulphenyl)-8-azabicyclo[3.2.1]oct-3-ene (40)

Enone 28 (600 mg, 1.71 mmol) was dissolved in a solution of CeCl$_3$.7H$_2$O (700 mg, 1.88 mmol) in MeOH (10 mL), then NaBH$_4$ (71 mg, 1.88 mmol) was added portion-wise. This mixture was stirred at RT for 15 min, then concentrated under reduced pressure, diluted with water (30 mL) and extracted with EtOAc (3×30 mL). The combined organic phase was washed with brine (50 mL), dried and concentrated under reduced pressure to afford the allylic alcohol intermediate (620 mg).

To a solution of the crude alcohols (620 mg) in pyridine (6 mL) was added Ac$_2$O (2 mL). The resulting solution was stirred at RT for 15 h, then concentrated under reduced pressure, diluted with EtOAc (50 mL), and washed with NH$_4$Cl (2×40 mL). Drying and concentration under reduced pressure afforded a crude mixture of the allylic acetates (660 mg, 97%) that was used in the next step without purification.

Phosphorous trichloride (0.85 mL, 9.71 mmol) was added to a solution of the sulphoxide intermediate (660 mg) in dry DMF (15 mL) at 0° C. After being stirred at 0° C. for 1 h, the reaction was quenched with a saturated solution of NaHCO$_3$ (60 mL) and extracted with ether (2×50 mL). The collected organic phase was washed with water (50 mL), brine (50 mL), dried and concentrated under reduced pressure. The crude residue was purified by flash chromatography on silica gel using EtOAc/hexane as eluent to afford the compound 40 (570 mg, 88%) as a mixture 3/1 of two isomers. R$_f$0.7 (EtOAc/hexane 3/7). Major isomer: $^1$H NMR (CDCl$_3$) δ1.91 (s, 3H), 2.34 (s, 3H), 2.72 (s, 3H), 6.23 (d, 1H, J=5.1 Hz), 6.33 (d, 1H, J=4.8 Hz); Minor isomer $^1$H NMR (CDCl$_3$) δ1.94 (s, 3H), 2.32 (s, 3H), 2.61 (s, 3H), 5.39 (s, 1H), 6.37 (d, 1H, J=5.7 Hz).

d. N-Methyl (1S,5S,7R)-3-phenyl-2β-n-propyl-6δ-(p-tolylsulphenyl)-8-azabicyclo[3.2.1]oct-3-ene (42)

To a suspension of CuCN (27 mg, 0.3 mmol) in dry ether (2 mL) at −7° C. was added n-PrMgBr (3.0 mL, 1.0 M in ether). After 10 min, a solution of 40 (570 mg, 1.5 mmol) in dry ether (5 mL) was added dropwise. The resulting mixture was stirred at RT for 1.5 h and then diluted with ether (20 mL). The organic phase was washed with a saturated solution of NH$_4$Cl (2×20 mL), dried, and concentrated under reduced pressure. The crude mixture was purified by flash chromatography on silica gel using EtOAc/hexane as eluent to afford the compound 42 (420 mg, 77%) as a colorless oil: [α]$^{25}_D$ +70° (c 1.5, acetone); R$_f$0.7 (EtOAc/hexane 3/7); $^1$H NMR (CDCl$_3$) δ0.78 (t, 3H, J=7.2 Hz), 1.1–1.6 (m, 4H), 2.2–2.3 (m, 1H), 2.34 (s, 3H), 2.4–2.5 (m, 2H), 2.63 (s, 3H), 3.37 (br s, 1H), 3.51 (t, 1H, J=7.8 Hz), 3.60 (t, 1H, J=5.1 Hz), 6.10 (d, 1H, J=5.4 Hz), 7.13 (d, 2H, J=8.1 Hz), 7.2–7.3 (m, 7H); $^{13}$C NMR (CDCl$_3$) δ13.9, 21.0, 21.1, 34.3, 40.0, 42.1, 47.1, 49.7, 62.3, 70.5, 126.0, 127.1, 128.3, 129.6, 129.7, 130.0, 134.0, 136.2, 138.4, 140.2.

Example 16
(1R,5S)-2βn-propyl-3α-phenyltropane (47)

The title compound was isolated from the chromatography of Example 15 as a colorless oil: [α]$^{25}_D$ −50° (c 1.0, CH$_2$Cl$_2$), $^1$H NMR (CDCl$_3$) δ0.77 (t, 3H, J=7.5 Hz), 1.0–1.6 (m, 8H), 2.0–2.3 (m, 2HO, 2.23 (s, 3H), 2.32–2.6 (m, 2H), 2.95 (d, 1H, J=6.0 Hz), 3.21 (bt, 1H, J=7.5 Hz), 7.1–7.35 (m, 5H); $^{13}$C NMR (CDCl$_3$) δ14.2, 19., 29.0, 29.5, 37.0, 40.6, 41.6, 41.8, 50.6, 59.5, 65.0, 125.7, 128.1, 128.2, 146.2; MS m/z (%) 243 (M$^+$, 5), 214 (3), 96 (42), 83 (100).

Example 17
(1R,5S)-2β-Phenyl-3β-phenyltropane (48)

Using a procedure similar to that described in Example 15, except replacing the compound 42 used therein with compound 43, compounds 48 and 49 were prepared and separated by chromatography to give the title compound as a colorless oil: [α]$^{25}_D$ −76° (c 1.0, CH$_2$Cl$_2$); $^1$H NMR (CDCl$_3$) δ1.64 (dt, 1H, J=4.2 and 13.5 Hz), 1.72–1.86 (m, 2H), 2.06–2.30 (m, 2H), 2.25 (s, 3H), 2.39 (dt, 1H, J=2.4 and 12.9 Hz), 2.84–2.92 (m, 1H), 3.26–3.42 (m, 3H), 6.85 (d, 2H, J=8.1 Hz), 6.95–7.12 (m, 5H), 7.35–7.45 (m, 2H); $^{13}$C NMR (CDCl$_3$) δ25.1, 27.3, 35.2, 37.5, 42.0, 53.3, 61.9. 67.7, 125.4, 125.5, 127.0, 127.5, 128.0, 130.6, 142.8, 143.2.

The intermediate compound 43 was prepared as follows.
a. N-Methyl (1S,5S,7R)-2,3-(di-phenyl)-6β-(p-tolylsulphenyl)-8-azabicyclo[3.2.1]oct-3-ene (43)

Using a procedure similar to that described in Example 15, sub-part d, except replacing the n-PrMgBr used therein with PhMgBr, the compound 43 was prepared as a colorless oil: $^1$H NMR (CDCl$_3$) δ2.3–2.4 (m, 1H), 2.37 (s, 3H), 2.43 (s, 3H), 2.52 (dd, 1H, J=8.1 and 12.3 Hz), 3.40 (s, 1H), 3.67 (t, 1H, J=7.5 Hz), 3.75 (br s, 1H), 6.51 (d, 1H, J=5.7 Hz), 7.0–7.5 (m, 14H).

Example 18
(1R,5S)-2β-Phenyl-3α-phenyltropane (49)

The title compound was isolated from the chromatography of Example 17 as a colorless oil; [α]$^{25}_D$ −55° (c 0.2, CH$_2$Cl$_2$); $^1$H NMR (CDCl$_3$) δ1.38 (t, 1H, J=13.2, 1.54–1.80 (m, 2H), 2.16–2.40 (m, 2H), 2.35 (s, 3H), 2.44–2.60 (m, 2H), 2.96–3.10 (m, 1H), 3.32 (d, 1H, J=6.3 Hz), 3.36–3.46 (m, 1H), 6.98 (d, 2H, J=8.1 Hz), 7.00–7.20 (m, 8H); $^{13}$C NMR (CDCl$_3$) δ29.7, 29.8, 40.9, 41.3, 43.6, 58.7, 59.5, 68.1, 125.7, 125.8, 127.3, 127.9, 128.0, 128.3, 144.6, 147.5.

Example 19
N-Methyl (1S,5S,7R)-2β-phenyl-3-(p-tolyl)tropane (50)

Using a procedure similar to that described in Example 15, except replacing the compound 42 used therein with compound 46, the title compound 50 was prepared as a colorless oil: [α]$^{25}_D$ −160° (c 0.2, CH$_2$Cl$_2$); $^1$H NMR (CDCl$_3$) δ1.62 (dt, 1H, J=4.2 and 13.5 Hz), 1.72–1.86 (m, 2H), 2.04–2.30 (m, 2H), 2.17 (s, 3H), 2.23 (s, 3H), 2.36 (dt, 1H, J=2.4 and 12.9 Hz), 2.84–2.92 (m, 1H), 3.24–3.42 (m, 3H), 6.74 (d, 2H, J=8.1 Hz), 6.85 (d, 2H, J=8.1 Hz), 7.00–7.15 (m, 3H), 7.37–7.45 (m, 2H); $^{13}$C NMR (CDCl$_3$) δ20.9, 25.1, 27.3, 35.5, 37.0, 42.0, 53.2, 62.0, 67.8, 125.4, 127.0, 127.8, 128.2, 130.7, 134.8, 140.1, 143.0; MS m/z (%) 291 (M$^+$, 8), 178 (4), 96 (60), 82 (100).

The intermediate compound 46 was prepared as follows.
a. N-Methyl (1S,5S,6R)-2-acetoxy-3-(p-tolyl)-6β-(p-tolylsulphenyl)-8-azabicyclo[3.2.1]oct-3-ene (41)

Using a procedure similar to that described in Example 15, sub-part c, except replacing the compound 28 used therein with compound 29, the compound 41 was prepared as a mixture 3/1 of two isomers. R$_f$0.7 (EtOAc/hexane 3/7). Major isomer (α-acetoxy derivatives): 1H NMR (CDCl$_3$) δ1.92 (s, 3H), 2.34 (s, 3H), 1.90–2.06 (m, 1H), 2.33 (s, 3H), 2.34 (s, 3H), 2.72 (s, 3H), 2.65–2.80 (m, 1H), 3.43 (d, 1H, J=5.1 Hz), 3.65–3.84 (m, 2H), 6.20 (d, 1H, J=5.1 Hz), 6.32 (d, 1H, J=4.5 Hz), 7.05–7.20 (m, 6H), 7.31 (d, 2H, J=7.8 Hz); Minor isomer (β-acetoxy derivatives): $^1$H NMR (CDCl$_3$) δ1.96 (s, 3H), 2.10–2.25 (m, 1H), 2.33 (s, 3H), 2.34 (s, 3H), 2.60 (s, 3H), 3.50–65 (m, 3H), 5.38 (s, 3H), 6.33 (d, 1H, J=5.4 Hz), 7.05–7.30 (m, 8H).

b. N-Methyl (1S,5S,7R)-2β-phenyl-3-(p-tolyl)-6β-(p-tolylslulphenyl)-8-azabicyclo[3.2.1]oct-3-ene (46)

Using a procedure similar to that described in Example 15, sub-part d, except replacing the compound 40 used therein with compound 41, and replacing the n-PrMgBr used therein with PhMgBr, the compound 46 was prepared as a colorless oil; $^1$H NMR (CDCl$_3$) δ2.20–2.35 (m, 1H), 2.22 (s, 3H), 2.37 (s, 3H), 2.42 (s, 3H), 2,50 (dd, 1H, J=8.4 and 12.6 Hz), 3.39 (s, 1H), 3.67 (t, 1H, J=8.4 Hz), 3.66–3.78 (m, 2H), 6.48 (d, 1H, J=5.4 Hz), 6.96 (d, 2H, J=8.1 Hz), 7.00–7.30 (m, 9H), 7.36 (d, 2H, J=8.1 Hz); $^{13}$C NMR (CDCl$_3$) δ21.0, 21.1, 40.1, 41.7, 49.8, 52.9, 62.2, 75.6, 115.3, 120.2, 125.4, 125.8, 127.9, 128.1, 128.9, 129.8, 130.2, 130.5, 133.9, 134.0, 136.4, 136.7, 142.7.

Example 20

N-Methyl (1S,5S,7R)-2β-n-propyl-3β-(p-tolyl)tropane (51)

Using a procedure similar to that described in Example 15, except replacing the compound 42 used therein with compound 44, the title compound 51 was prepared as a colorless oil: $^1$H NMR (CDCl$_3$) δ0.78 (t, 3H, J=7.2 Hz), 1.08–1.56 (m, 8H), 2.04–2.24 (m, 2H), 2.23 (s, 3H), 2.30 (s, 3H), 2.28–2.58 (m, 2H), 2.94 (d, 1H, J=6.3 Hz), 3.19 (t, 1H, J=7.8 Hz), 7.06 (s, 4H); $^{13}$C NMR (CDCl$_3$) δ14.2, 19.9, 21.0, 29.0, 29.5, 37.0, 40.1, 41.6, 41.9, 50.6, 59.6, 64.9, 128.1, 128.8, 135.1, 143.1.

The intermediate compound 44 was prepared as follows.

a. N-Methyl (1S,5S,7R)-2β-n-propyl-3-(p-tolyl)-6β-(p-tolylsulphenyl)-8-azabicyclo[3.2.1]oct-3-ene (44)

Using a procedure similar to that described in Example 15, sub-part d, except replacing the compound 40 used therein with compound 41, the title compound 44 was prepared as a colorless oil: $[α]^{25}{}_D$ +110° (c 2.6, CH$_2$Cl$_2$); R$_f$0.5 (EtOAc/hexane, 1/4); $^1$H NMR (CDCl$_3$) δ0.81 (t, 3H, J=7.2 Hz), 1.2–1.6 (m, 4H), 2.2–2.3 (m, 1H), 2.35 (s, 3H), 2.4–2.5 (m, 2H), 2.65 (s, 3H), 3.39 (br s, 1H), 3.53 (t, 1H, J=7.8 Hz), 3.60 (t, 1H, J=5.4 Hz), 6.08 (d, 1H, J=6.0 Hz), 7.10–7.24 (m, 6H); 7.32 (d, 2H, J=8.1 Hz); $^{13}$C NMR (CDCl$_3$) δ14.0, 21.0, 21.1, 34.3, 40.0, 42.1, 47.1, 49.7, 62.3, 70.6, 125.8, 128.8, 129.0, 129.7, 129.9, 134.1, 136.1, 136.9, 137.3, 138.2.

Example 21

N-Methyl (1S,5S,7R)-2β-n-butyl-3α-(p-tolyl)tropane (52)

Using a procedure similar to that described in Example 15, except replacing the compound 42 used therein with compound 45, the title compound 52 was prepared as a colorless oil: $[α]^{25}{}_D$ −42° (c 0.5, CH$_2$Cl$_2$); $^1$H NMR (CDCl$_3$) δ0.80 (t, 3H, J=6.6 Hz), 1.08–1.56 (m, 10H), 2.04–2.24 (m, 2H), 2.23 (s, 3H), 2.30 (s, 3H), 2.28–2.58 (m, 2H), 2.94 (d, 1H, J=6.0 Hz), 3.19 (t, 1H, J=7.8 Hz), 7.06 (s, 4H); $^{13}$C NMR (CDCl$_3$) δ14.1, 20.9, 22.8, 28.9, 29.0, 29.5, 34.3, 40.0, 41.6, 41.8, 50.8, 59.5, 64.9, 128.1, 128.8, 135.1, 143.1.

The intermediate compound 45 was prepared as follows.

a. N-Methyl (1S,5S,7R)-2β-n-butyl-3-(p-tolyl)-6β-(p-tolylsulphenyl)-8-azabicyclo[3.2.1]oct-3-ene (45)

Using a procedure similar to that described in Example 15, sub-part d, except replacing the compound 40 used therein with compound 41, and replacing the n-BuMgBr with n-PrMgBr, the compound 45 was prepared as a colorless oil: $[α]^{25}{}_D$ +79° (c 1.0, EtOH); $^1$H NMR (CDCl$_3$) δ0.80 (t, 3H, J=6.6 Hz), 1.00–1.40 (m, 5H), 1.40–1.60 (m, 1H), 2.20–2.50 (m, 3H), 2.32 (s, 3H), 2.33 (s, 3H), 2.63 (s, 3H), 3.35 (s, 1H), 3.50 (t, 1H, J=7.2 Hz), 3.58 (t, 1H, J=5.1 Hz), 6.06 (d, 1H, J=5.4 Hz), 7.00–7.20 (m, 6H), 7.31 (d, 2H, J=8.1 Hz); $^{13}$C NMR (CDCl$_3$) δ14.0, 20.9, 21.0, 22.5, 30.3, 31.7, 39.9, 42.1, 47.3, 49.8, 62.3, 70.4, 125.8, 128.7, 129.0, 129.7, 130.2, 134.0, 136.2, 136.8, 137.2, 138.2.

Example 22

Synthesis of Ethyl 8-Methyl-2-oxo-3-phenyl-8-azabicyclo[3.2.1]oct-3-ene-6-carboxylate and Ethyl 8-methyl-2-oxo-3-phenyl-8-azabicyclo[3.2.1]oct-3-ene-7-carboxylate (6a–d)

Using a procedure similar to that described in Example 7, except replacing the phenyl vinylsulfone used therein with methyl acrylate, compounds 6a–6d were prepared as a mixture of four isomers and separated by silica gel column chromatography using EtOAc/n-hexane as eluant. 6a (33%): dark yellow oil; R$_f$=0.70 (EtOAc/n-hexane 1/1); $^1$H NMR (CDCl$_3$) δ1.312 (t, 3H, J=6.9 Hz), 1.99 (dd, H$_{7endo}$, J$_{7en\text{-}6}$=9.9 Hz, J$_{7en\text{-}7ex}$=14.1 Hz), 2.52 (s, 3H), 2.90 (qd, H$_{7exo}$, J$_{7ex\text{-}6}$=3.6 Hz, J$_{7ex\text{-}6}$=7.8 Hz, J$_{7ex\text{-}7en}$=13.8 Hz), 3.02 (dd, H$_6$, J$_{6\text{-}7ex}$=3.6 Hz, J$_{6\text{-}7en}$=9.0 Hz), 3.74 (d, H$_5$, J$_{5\text{-}4}$=7.5 Hz), 4.23 (q, 2H, J=7.2 Hz), 7.07 (d, H$_4$, J$_{4\text{-}5}$=5.4 Hz), 7.3–7.4 (m, 5H); $^{13}$C NMR (CDCl$_3$) δ14.20, 27.84, 35.83, 47.52, 61.44, 63.61, 70.72, 128.23, 128.28, 133.95, 137.93, 143.61, 172.83, 197.86. 6b (26%): yellow oil; R$_f$=0.4 (EtOAc/n-hexane 1/1); $^1$H NMR (CDCl$_3$) δ1.25 (t, 3H, J=7.2 Hz), 2.11 (dd, H$_{7endo}$, J$_{7en\text{-}6}$=6.0 Hz, J$_{7en\text{-}7ex}$=14,4 Hz), 2.48 (s, 3H), 2.64 (qd, H$_{7exo}$, J$_{7ex\text{-}1}$=7.8 Hz, J$_{7ex\text{-}6}$=10.2 Hz, J$_{7ex\text{-}7en}$=13.8 Hz), 3.60 (dt, H$_6$, J$_{6\text{-}5}$=J$_{6\text{-}7en}$=5.7 Hz, J$_{6\text{-}7ex}$=10.5 Hz), 3.70 (d, H$_1$, J$_{1\text{-}7ex}$=8.1 Hz), 4.20 (d, H$_5$, J$_{5\text{-}4}$=J$_{5\text{-}6}$=5.4 Hz), 6.98 (d, H$_4$, J$_{4\text{-}5}$=5.1 Hz), 7.34 (bs, 5H). 6c (20%): pale yellow oil; R$_f$=0.6 (EtOAc/n-hexane 1/1); $^1$H NMR (CDCl$_3$) δ1.30 (t, 3H, J=7.2 Hz), 2.22 (dd, H$_{6endo}$, J$_{6en\text{-}7}$=9.6 Hz, J$_{6en\text{-}6ex}$=12.6 Hz), 2.795 (dt, H$_{6exo}$, J$_{6ex\text{-}5}$=J$_{6ex\text{-}7}$=6.3 Hz, J$_{6ex\text{-}6en}$=12.6 Hz), 3.534 (dd, H$_7$, J$_{7\text{-}6ex}$=6.6 Hz, J$_{7\text{-}6en}$=9.3 Hz), 3.97 (t, H$_5$, J$_{5\text{-}4}$=J$_{5\text{-}6}$=5.7 Hz), 4.01 (s, H$_1$), 7.08 (d, H$_4$, J$_{4\text{-}5}$=5.4 Hz), 7.36 (bs, 5H); $^{13}$C NMR (CDCl$_3$) δ14.18, 32.45, 37.10, 43.39, 61.49, 61.65, 74.17, 128.20, 128.26, 129.87, 132.90, 134.03, 136.83, 146.61, 173.43, 195.92. 6d (12%): pale yellow oil; R$_f$=0.35 (EtOAc/n-hexane 1/1); $^1$H NMR (CDCl$_3$) δ1.20 (t, 3H, J=7.2 Hz), 2.30 (dd, H$_{6endo}$, J$_{6en\text{-}7}$=3.9 Hz, J$_{6en\text{-}6ex}$=12.3 Hz), 2.47 (s, 3H), 2.52 (qd, H$_{6exo}$, J$_{6ex\text{-}5}$=6.6 Hz, J$_{6ex\text{-}7}$=10.5 Hz, J$_{6ex\text{-}6en}$=12.4 Hz), 3.64 (m, H$_7$), 3.87 (t, H$_5$, J$_{5\text{-}4}$=J$_{5\text{-}6ex}$=6.0 Hz), 3.95 (d, H$_1$, J$_{1\text{-}7}$=7.2 Hz), 4.07 (q, 2H, J=7.2 Hz), 7.11 (d, H$_4$, J$_{4\text{-}5}$=5.7 Hz), 7.33 (bs, 5H).

Example 26

The following illustrate representative pharmaceutical dosage forms, containing a compound of formula I ('Compound X'), for therapeutic or prophylactic use in mammals such as humans.

| (i) Tablet 1 | mg/tablet |
| --- | --- |
| 'Compound X' | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |

| (ii) Tablet 2 | mg/tablet |
| --- | --- |
| 'Compound X' | 20.0 |
| Microcrystalline cellulose | 410.0 |
| Starch | 50.0 |
| Sodium starch glycolate | 15.0 |
| Magnesium stearate | 5.0 |
| | 500.0 |

| (iii) Capsule | mg/capsule |
|---|---|
| 'Compound X' | 10.0 |
| Colloidal silicon dioxide | 1.5 |
| Lactose | 465.5 |
| Pregelatinized starch | 120.0 |
| Magnesium stearate | 3.0 |
| | 600.0 |

| (iv) Injection 1 (1 mg/ml) | mg/ml |
|---|---|
| 'Compound X' (free acid form) | 1.0 |
| Dibasic sodium phosphate | 12.0 |
| Monobasic sodium phosphate | 0.7 |
| Sodium chloride | 4.5 |
| 1.0 N Sodium hydroxide solution (pH adjustment to 7.0–7.5) | q.s. |
| Water for injection | q.s. ad 1 mL |

| (v) Injection 2 (10 mg/ml) | mg/ml |
|---|---|
| 'Compound X' (free acid form) | 10.0 |
| Monobasic sodium phosphate | 0.3 |
| Dibasic sodium phosphate | 1.1 |
| Polyethylene glycol 400 | 200.0 |
| 01 N Sodium hydroxide solution (pH adjustment to 7.0–7.5) | q.s. |
| Water for injection | q.s. ad 1 mL |

| (vi) Aerosol | mg/can |
|---|---|
| 'Compound X' | 20.0 |
| Oleic acid | 10.0 |
| Trichloromonofluoromethane | 5,000.0 |
| Dichlorodifluoromethane | 10,000.0 |
| Dichlorotetrafluoroethane | 5,000.0 |

The above formulations may be obtained by conventional procedures well known in the pharmaceutical art.

The invention has been described with reference to various specific and preferred embodiments and techniques. However, it should be understood that many variations and modifications may be made while remaining within the spirit and scope of the invention.

What is claimed is:

1. A compound of formula (I):

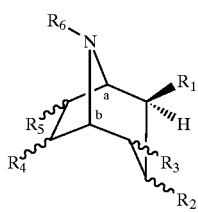

(I)

wherein $R_1$ is $OR_7$;

$R_2$ is aryl or aryl($C_1$–$C_4$)alkyl;

$R_3$ is hydrogen, ($C_1$–$C_4$)alkyl, ($C_2$–$C_4$)alkenyl or ($C_2$–$C_4$)alkynyl;

$R_4$ and $R_5$ are independently hydrogen, halo, CN, $OR_9$, $COOR_{10}$, arylSO$_2$—, or —CH$_2$NHR$_{11}$;

$R_6$ is hydrogen, ($C_1$–$C_4$)alkyl, ($C_1$–$C_4$)alkenyl, ($C_1$–$C_4$)alkynyl, aryl, or aryl($C_1$–$C_4$)alkyl;

$R_7$ is hydrogen, ($C_1$–$C_4$)alkyl, ($C_1$–$C_5$)alkanoyl, arylcarbonyl, or aryl ($C_1$–$C_5$)alkanoyl;

each $R_8$ is independently hydrogen, ($C_1$–$C_4$)alkyl, ($C_1$–$C_4$)alkanoyl, aryl, aryl($C_1$–$C_4$)alkyl, or arylcarbonyl;

$R_9$ is hydrogen, ($C_1$–$C_4$)alkyl, ($C_1$–$C_5$)alkanoyl, or arylcarbonyl;

$R_{10}$ is hydrogen or ($C_1$–$C_4$)alkyl; and $R_{11}$ is hydrogen or ($C_1$–$C_4$)alkyl;

wherein any aryl in $R_1$, $R_2$, and $R_6$–$R_9$ may optionally be substituted with 1, 2, or 3 substituents independently selected from the group consisting of halo, CF$_3$, ($C_1$–$C_4$)alkoxy, ($C_1$–$C_4$)alkyl, ($C_1$–$C_4$)alkenyl, ($C_1$–$C_4$)alkynyl, amino, nitro, cyano, and aryl;

or a pharmaceutically acceptable salt thereof.

2. A compound of formula (I):

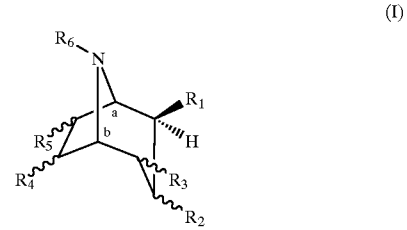

(I)

wherein $R_1$ is hydrogen, $OR_7$, or $N(R_8)_2$;

$R_2$ is aryl or aryl($C_1$–$C_4$)alkyl;

$R_3$ is hydrogen, ($C_1$–$C_4$)alkyl, ($C_2$–$C_4$)alkenyl or ($C_2$–$C_4$)alkynyl;

$R_4$ and $R_5$ are independently hydrogen, halo, CN, $OR_9$, $COOR_{10}$, arylSO$_2$—, or —CH$_2$NHR$_{11}$;s $R_6$ is hydrogen, ($C_1$–$C_4$)alkyl, ($C_1$–$C_4$)alkenyl, ($C_1$–$C_4$)alkynyl, aryl, or aryl($C_1$–$C_4$)alkyl;

$R_7$ is hydrogen, ($C_1$–$C_4$)alkyl, ($C_1$–$C_5$)alkanoyl, arylcarbonyl, or aryl ($C_1$–$C_5$)alkanoyl;

each $R_8$ is independently hydrogen, ($C_1$–$C_4$)alkyl, ($C_1$–$C_4$)alkanoyl, aryl, aryl($C_1$–$C_4$)alkyl, or arylcarbonyl;

$R_9$ is hydrogen, ($C_1$–$C_4$)alkyl, ($C_1$–$C_5$)alkanoyl, or arylcarbonyl;

$R_{10}$ is hydrogen or ($C_1$–$C_4$)alkyl; and $R_{11}$ is hydrogen or ($C_1$–$C_4$)alkyl;

wherein any aryl in $R_1$, $R_2$, and $R_6$–$R_9$ may optionally be substituted with 1, 2, or 3 substituents independently selected from the group consisting of halo, CF$_3$, ($C_1$–$C_4$)alkoxy, ($C_1$–$C_4$)alkyl, ($C_1$–$C_4$)alkenyl, ($C_1$–$C_4$)alkynyl, amino, nitro, cyano, and aryl;

or a pharmaceutically acceptable salt thereof.

3. A compound of formula (I):

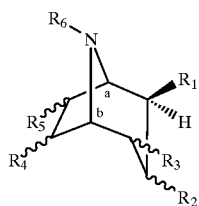

(I)

wherein
- $R_1$ is $OR_7$, or $N(R_8)_2$;
- $R_2$ is aryl or aryl($C_1$–$C_4$)alkyl;
- $R_3$ is hydrogen, ($C_1$–$C_4$)alkyl, ($C_2$–$C_4$)alkenyl or ($C_2$–$C_4$)alkynyl;
- $R_4$ and $R_5$ are independently hydrogen, halo, CN, $OR_9$, $COOR_{10}$, arylSO$_2$—, or —CH$_2$NHR$_{11}$;
- $R_6$ is hydrogen, ($C_1$–$C_4$)alkyl, ($C_1$–$C_4$)alkenyl, ($C_1$–$C_4$)alkynyl, aryl, or aryl($C_1$–$C_4$)alkyl;
- $R_7$ is hydrogen, ($C_1$–$C_4$)alkyl, ($C_1$–$C_5$)alkanoyl, arylcarbonyl, or aryl ($C_1$–$C_5$)alkanoyl;
- each $R_8$ is independently hydrogen, ($C_1$–$C_4$)alkyl, ($C_1$–$C_4$)alkanoyl, aryl, aryl($C_1$–$C_4$)alkyl, or arylcarbonyl;
- $R_9$ is hydrogen, ($C_1$–$C_4$)alkyl, ($C_1$–$C_5$)alkanoyl, or arylcarbonyl;
- $R_{10}$ is hydrogen or ($C_1$–$C_4$)alkyl; and
- $R_{11}$ is hydrogen or ($C_1$–$C_4$)alkyl;
- wherein any aryl in $R_1$, $R_2$, and $R_6$–$R_9$ may optionally be substituted with 1, 2, or 3 substituents independently selected from the group consisting of halo, CF$_3$, ($C_1$–$C_4$)alkoxy, ($C_1$–$C_4$)alkyl, ($C_1$–$C_4$)alkenyl, ($C_1$–$C_4$)alkynyl, amino, nitro, cyano, and aryl;

or a pharmaceutically acceptable salt thereof.

4. A compound of formula (I):

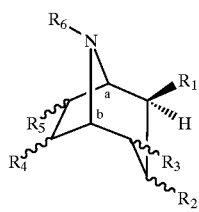

(I)

wherein
- $R_1$ is hydrogen, $OR_7$, or $N(R_8)_2$;
- $R_2$ is aryl or aryl($C_1$–$C_4$)alkyl; wherein the aryl is substituted with 1, 2, or 3 substituents independently selected from the group consisting of halo, CF$_3$, ($C_1$–$C_4$)alkoxy, ($C_1$–$C_4$)alkenyl, ($C_1$–$C_4$)alkynyl, amino, nitro and cyano;
- $R_3$ is hydrogen, ($C_1$–$C_4$)alkyl, ($C_2$–$C_4$)alkenyl or ($C_2$–$C_4$)alkynyl;
- $R_4$ and $R_5$ are independently hydrogen, halo, CN, $OR_9$, $COOR_{10}$, arylSO$_2$—, or —CH$_2$NHR$_{11}$;
- $R_6$ is hydrogen, ($C_1$–$C_4$)alkyl, ($C_1$–$C_4$)alkenyl, ($C_1$–$C_4$)alkynyl, aryl, or aryl($C_1$–$C_4$)alkyl;
- $R_7$ is hydrogen, ($C_1$–$C_4$)alkyl, ($C_1$–$C_5$)alkanoyl, arylcarbonyl, or aryl ($C_1$–$C_5$)alkanoyl;
- each $R_8$ is independently hydrogen, ($C_1$–$C_4$)alkyl, ($C_1$–$C_4$)alkanoyl, aryl, aryl($C_1$–$C_4$)alkyl, or arylcarbonyl;
- $R_9$ is hydrogen, ($C_1$–$C_4$)alkyl, ($C_1$–$C_5$)alkanoyl, or arylcarbonyl;
- $R_{10}$ is hydrogen or ($C_1$–$C_4$)alkyl; and
- $R_{11}$ is hydrogen or ($C_1$–$C_4$)alkyl;
- wherein any aryl in $R_2$, and $R_6$–$R_9$ may optionally be substituted with 1, 2, or 3 substituents independently selected from the group consisting of halo, CF$_3$, ($C_1$–$C_4$)alkoxy, ($C_1$–$C_4$)alkyl, ($C_1$–$C_4$)alkenyl, ($C_1$–$C_4$)alkynyl, amino, nitro, cyano, and aryl;

or a pharmaceutically acceptable salt thereof.

5. A compound of formula (I):

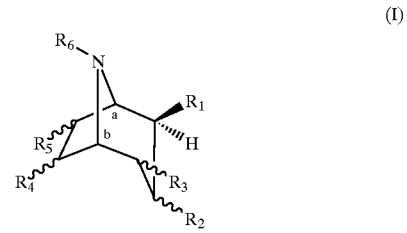

(I)

wherein
- $R_1$ is hydrogen, aryl, aryl($C_1$–$C_4$)alkyl, ($C_1$–$C_4$)alkyl, $OR_7$, or $N(R_8)_2$;
- $R_2$ is aryl or aryl($C_1$–$C_4$)alkyl;
- $R_3$ is ($C_1$–$C_4$)alkyl, ($C_2$–$C_4$)alkenyl or ($C_2$–$C_4$)alkynyl;
- $R_4$ and $R_5$ are independently hydrogen, halo, CN, $OR_9$, $COOR_{10}$, arylSO$_2$—, or —CH$_2$NHR$_{11}$;
- $R_6$ is hydrogen, ($C_1$–$C_4$)alkyl, ($C_1$–$C_4$)alkenyl, ($C_1$–$C_4$)alkynyl, aryl, or aryl($C_1$–$C_4$)alkyl;
- $R_7$ is hydrogen, ($C_1$–$C_4$)alkyl, ($C_1$–$C_5$)alkanoyl, arylcarbonyl, or aryl ($C_1$–$C_5$)alkanoyl;
- each $R_8$ is independently hydrogen, ($C_1$–$C_4$)alkyl, ($C_1$–$C_4$)alkanoyl, aryl, aryl($C_1$–$C_4$)alkyl, or arylcarbonyl;
- $R_9$ is hydrogen, ($C_1$–$C_4$)alkyl, ($C_1$–$C_5$)alkanoyl, or arylcarbonyl;
- $R_{10}$ is hydrogen or ($C_1$–$C_4$)alkyl; and
- $R_{11}$ is hydrogen or ($C_1$–$C_4$)alkyl;
- wherein any aryl in $R_1$, $R_2$, and $R_6$–$R_9$ may optionally be substituted with 1, 2, or 3 substituents independently selected from the group consisting of halo (preferably I or Cl), CF$_3$, ($C_1$–$C_4$)alkoxy, ($C_1$–$C_4$)alkyl, ($C_1$–$C_4$)alkenyl, ($C_1$–$C_4$)alkynyl, amino, nitro, cyano, and aryl;

or a pharmaceutically acceptable salt thereof.

6. The compound of claim 5 wherein $R_3$ is ($C_2$–$C_4$)alkenyl or ($C_2$–$C_4$)alkynyl.

7. The compound of claim 5 wherein $R_3$ is ($C_1$–$C_4$)alkyl or ($C_2$–$C_4$)alkynyl.

8. A compound of formula (I):

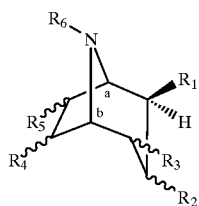

(I)

wherein $R_1$ is $OR_7$;

$R_2$ is aryl or aryl$(C_1-C_4)$alkyl;

$R_3$ is hydrogen, $(C_1-C_4)$alkyl, $(C_2-C_4)$alkenyl or $(C_2-C_4)$alkynyl;

$R_4$ and $R_5$ are independently hydrogen, halo, CN, $OR_9$, $COOR_{10}$, arylSO$_2$—, or —CH$_2$NHR$_{11}$;

$R_6$ is hydrogen, $(C_1-C_4)$alkyl, $(C_1-C_4)$alkenyl, $(C_1-C_4)$alkynyl, aryl, or aryl$(C_1-C_4)$alkyl;

$R_7$ is $(C_1-C_5)$alkanoyl, arylcarbonyl, or aryl $(C_1-C_5)$alkanoyl, each $R_8$ is independently hydrogen, $(C_1-C_4)$alkyl, $(C_1-C_4)$alkanoyl, aryl, aryl$(C_1-C_4)$alkyl, or arylcarbonyl;

$R_9$ is hydrogen, $(C_1-C_4)$alkyl, $(C_1-C_5)$alkanoyl, or arylcarbonyl;

$R_{10}$ is hydrogen or $(C_1-C_4)$alkyl; and $R_{11}$ is hydrogen or $(C_1-C_4)$alkyl;

wherein any aryl in $R_1$, $R_2$, and $R_6$–$R_9$ may optionally be substituted with 1, 2, or 3 substituents independently selected from the group consisting of halo, $CF_3$, $(C_1-C_4)$alkoxy, $(C_1-C_4)$alkyl, $(C_1-C_4)$alkenyl, $(C_1-C_4)$alkynyl, amino, nitro, cyano, and aryl;

or a pharmaceutically acceptable salt thereof.

9. A compound of formula (I):

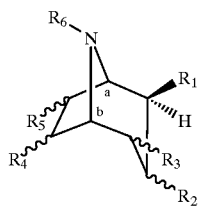

(I)

wherein $R_1$ is hydrogen, aryl, aryl$(C_1-C_4)$alkyl, $(C_1-C_4)$alkyl, $OR_7$, or $N(R_8)_2$;

$R_2$ is aryl or aryl$(C_1-C_4)$alkyl;

$R_3$ is hydrogen, $(C_1-C_4)$alkyl, $(C_2-C_4)$alkenyl or $(C_2-C_4)$alkynyl;

one of $R_4$ and $R_5$ is hydrogen, and the other is halo, CN, $OR_9$, $COOR_{10}$, arylSO$_2$—, or —CH$_2$NHR$_{11}$;

$R_6$ is hydrogen, $(C_1-C_4)$alkyl, $(C_1-C_4)$alkenyl, $(C_1-C_4)$alkynyl, aryl, or aryl$(C_1-C_4)$alkyl;

$R_7$ is hydrogen, $(C_1-C_4)$alkyl, $(C_1-C_5)$alkanoyl, arylcarbonyl, or aryl $(C_1-C_5)$alkanoyl;

each $R_8$ is independently hydrogen, $(C_1-C_4)$alkyl, $(C_1-C_4)$alkanoyl, aryl, aryl$(C_1-C_4)$alkyl, or arylcarbonyl;

$R_9$ is hydrogen, $(C_1-C_4)$alkyl, $(C_1-C_5)$alkanoyl, or arylcarbonyl;

$R_{10}$ is hydrogen or $(C_1-C_4)$alkyl; and $R_{11}$ is hydrogen or $(C_1-C_4)$alkyl;

wherein any aryl in $R_1$, $R_2$, and $R_6$–$R_9$ may optionally be substituted with 1, 2, or 3 substituents independently selected from the group consistng of halo (preferably I or Cl), $CF_3$, $(C_1-C_4)$alkoxy, $(C_1-C_4)$alkyl, $(C_1-C_4)$alkenyl, $(C_1-C_4)$alkynyl, amino, nitro cyano, and aryl;

or a pharmaceutically acceptable salt thereof.

10. The compound of any one of claims 1–9, wherein the carbon designated "a" has the (R) stereochemistry and the carbon designated "b" has the (S) stereochemistry.

11. The compound (1R,5S)-2β-phenyl-3α-(p-tolyl)tropane; or a pharmaceutically acceptable salt thereof.

12. A pharmaceutical composition comprising an effective amount of a compound of formula (I) or a pharmaceutically acceptable salt thereof as defined in any one of claims 1–9 in combination with a pharmaceutically acceptable diluent or carrier.

13. A compound of formula (XI):

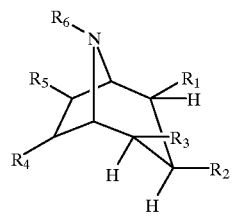

(XI)

wherein $R_1$ is $OR_7$ where $R_7$ is H, $(C_1-C_4)$alkyl, $(C_1-C_4)$alkylC(O)—, $(C_5-C_7)$arylC(O)—, or NHR$_8$ where $R_8$ is H, $(C_1-C_4)$alkyl, $(C_1-C_4)$alkyl(CO)— or $(C_5-C_7)$arylC(O)—;

$R_2$ is phenyl or benzyl, each optionally substituted with halo, $CF_3$, $(C_1-C_4)$alkoxy, $(C_1-C_4)$alkyl, $(C_1-C_4)$alkenyl, $(C_1-C_4)$alkynyl, amino, nitro or $(C_5-C_7)$aryl;

$R_5$ is $(C_1-C_4)$alkyl, $(C_1-C_4)$alkenyl or $(C_1-C_4)$alkynyl;

$R_4$ and $R_5$ are independently H, halo, CN, $OR_9$ where $R_9$ is H, $(C_1-C_4)$alkyl, $(C_1-C_4)$alkylC(O)—, $(C_5-C_7)$arylC(O)—; $COOR_{10}$ where $R_{10}$ is H or $(C_1-C_4)$alkyl; or CH$_2$NHR$_{11}$ where $R_{11}$ is H or $(C_1-C_4)$alkyl; and $R_6$ is H, $(C_1-C_4)$alkyl, $(C_1-C_4)$alkenyl, $(C_1-C_4)$alkynyl or benzyl; or a stereoisomer thereof; or a pharmaceutically acceptable salt thereof.

14. A compound of formula (XI):

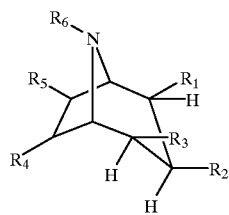

(XI)

wherein $R_1$ is H, $OR_7$ where $R_7$ is H, $(C_1-C_4)$alkyl, $(C_1-C_4)$alkylC(O)—, $(C_5-C_7)$arylC(O)—; or $NHR_8$ where $R_8$ is H, $(C_1-C_4)$alkyl, $(C_1-C_4)$alkyl(CO)— or $(C_5-C_7)$arylC(O)—;

$R_2$ is phenyl or benzyl, each optionally substituted with halo, $CF_3$, $(C_1-C_4)$alkoxy, $(C_1-C_4)$alkyl, $(C_1-C_4)$alkenyl, $(C_1-C_4)$alkynyl, amino, nitro or $(C_5-C_7)$aryl;

$R_3$ is $(C_1-C_4)$alkenyl or $(C_1-C_4)$alkynyl;

$R_4$ and $R_5$ are independently H, halo, CN, $OR_9$ where $R_9$ is H, $(C_1-C_4)$alkyl, $(C_1-C_4)$alkylC(O)—, $(C_5-C_7)$arylC(O)—; $COOR_{10}$ where $R_{10}$ is H or $(C_1-C_4)$alkyl; or $CH_2NHR_{11}$ where $R_{11}$ is H or $(C_1-C_4)$alkyl; and $R_6$ is H, $(C_1-C_4)$alkyl, $(C_1-C_4)$alkenyl, $(C_1-C_4)$alkynyl or benzyl; or a stereoisomer thereof; or a pharmaceutically acceptable salt thereof.

15. The compound of claim 14 wherein $R_2$ is phenyl.

16. The compound of claim 15 wherein the phenyl is substituted with I or Cl.

17. The compound of claim 14 wherein $R_6$ is $(C_1-C_4)$alkyl.

* * * * *